US012251476B2

(12) United States Patent
Lee et al.

(10) Patent No.: US 12,251,476 B2
(45) Date of Patent: Mar. 18, 2025

(54) MECHANO-SENSITIVE MICROCAPSULES FOR DRUG DELIVERY

(71) Applicant: The Trustees of the University of Pennsylvania, Philadelphia, PA (US)

(72) Inventors: Daeyeon Lee, Wynnewood, PA (US); Robert Leon Mauck, Philadelphia, PA (US); George R Dodge, Philadelphia, PA (US); Fuquan Tu, Philadelphia, PA (US); Bhavana Mohanraj, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 17/817,030

(22) Filed: Aug. 3, 2022

(65) Prior Publication Data
US 2023/0052488 A1 Feb. 16, 2023

Related U.S. Application Data

(63) Continuation of application No. 15/579,084, filed as application No. PCT/US2016/035220 on Jun. 1, 2016, now abandoned.

(60) Provisional application No. 62/169,286, filed on Jun. 1, 2015.

(51) Int. Cl.
| | | |
|---|---|---|
| *A61K 9/50* | (2006.01) | |
| *A61K 9/107* | (2006.01) | |
| *A61K 38/18* | (2006.01) | |
| *A61P 19/04* | (2006.01) | |
| *B01J 13/02* | (2006.01) | |
| *A61K 9/00* | (2006.01) | |

(52) U.S. Cl.
CPC .......... *A61K 9/5031* (2013.01); *A61K 9/1075* (2013.01); *A61K 9/5089* (2013.01); *A61K 38/1841* (2013.01); *A61P 19/04* (2018.01); *B01J 13/02* (2013.01); *A61K 9/0024* (2013.01)

(58) Field of Classification Search
None
See application file for complete search history.

(56) References Cited

U.S. PATENT DOCUMENTS

| | | |
|---|---|---|
| 2007/0098148 A1 | 5/2007 | Sherman |
| 2009/0286437 A1 | 11/2009 | Cunningham et al. |
| 2010/0268191 A1 | 10/2010 | Trudel et al. |
| 2011/0125080 A1 | 5/2011 | Shi et al. |
| 2011/0160698 A1 | 6/2011 | Hoffmann et al. |
| 2012/0093717 A1 | 4/2012 | Mauck et al. |
| 2012/0123321 A1 | 5/2012 | Silberg |
| 2012/0265300 A1 | 10/2012 | Mauck et al. |
| 2012/0328529 A1 | 12/2012 | Lee et al. |
| 2013/0029030 A1 | 1/2013 | Larsen |

OTHER PUBLICATIONS

Izawa, Hironori et al. "Patient-controlled drug delivery system utilizing mechanical stimuli-responsive gel carrier". Drug Delivery System. Mar. 25, 2013;28(2):92-8. Original article (Year: 2013).*
Izawa, Hironori et al. "Patient-controlled drug delivery system utilizing mechanical stimuli-responsive gel carrier". Drug Delivery System. Mar. 25, 2013;28(2):92-8. human translation (Year: 2013).*
Definition of endongeous from www.merriam-webster.com, accessed Sep. 5, 2023 (Year: 2023).*
Abbaspourrad et al., "Controlling Release from pH-Responsive Microcapsules", Langmuir, 2013, 29, pp. 12697-12702.
Anandhakumar S. et al., "Silver nanoparticles modified nanocapsules for ultrasonically activated drug delivery." Materials Science and Engineering: C, vol. 32, Issue 8, 2012, pp. 2349-2355.
Andreuccetti C. et al., "Effect of hydrophobic plasticizers on functional properties of gelatin-based films," Food Research International, vol. 42, Issue 8, 2009, pp. 1113-1121.
Bain et al., "Enchanced MSC Chondrogenesis Following delivery of TGF-B3 from Alginate Microspheres Within Hyaluronic Acid Hydrogels In Vitro and In Vivo", Biomaterials, 32, (2011) pp. 6425-6434.
Blaiszik et al., "Microcapsules Filled with Reactive Solutions for Self-Healing Materials", Polymer, 50 (2009) pp. 990-997.
Brugarolas et al., "Tailoring and Understanding the Mechanical Properties of Nanoparticle-Shelled Bubbles", ACS Applied Mater, Interfaces, 2014, 6, pp. 11558-11572.
Bussemer et al., "A Pulsatile Drug Delivery System Based on Rupturable Coated Hard Gelatin Capsules", Journal of Controlled Release, vol. 93, 2003, pp. 331-339.
Chen D, Wu J. An in vitro feasibility study of controlled drug release from encapsulated nanometer liposomes using high intensity focused ultrasound. Ultrasonics. Aug. 1, 2010 ;50(8):744-9. (Year: 2010).
Chen et al., "Designer Polymer-Based Microcapsules Made Using Microfluidics", Langmuir, 2012, 28, pp. 144-152.
Chun et al., "Biodegradable PLGA Microcarriers for Injectable Delivery of Chondrocytes: Effect of Surface Modification on Cell Attachment and Function", Biotechnol. Prog., 2004, 20, pp. 1797-1801.
Datta et al., "25th Anniversary Article: Double Emulsion Templated Solid Microcapsules: Mechanic and Controlled Release", Advanced Materials, 2014, 26, pp. 2205-2218.
Definition of "endogenous" from dictionary.com, accessed Sep. 29, 2020 (Year: 2020).
Definition of "rupture" from Wiktionary.org, accessed May 23, 2019 (Year: 2019).
Desai et al., "Active Self-Healing Encapsulation of Vaccine Antigens in PLGA Microspheres", Journal of Controlled Release, 165, (2013) pp. 62-74.
DiMicco et al., "Mechanisms and Kinetics of Glycosaminoglycan Release Following in Vitro Cartilage Injury", Arthritis & Rheumatism, vol. 50, No. 3, Mar. 2004, pp. 840-848.

(Continued)

*Primary Examiner* — Nissa M Westerberg
(74) *Attorney, Agent, or Firm* — BakerHostetler

(57) ABSTRACT

Embodiments of the present invention relate to mechanically-activated microcapsules (MAMCs) for controlled drug-delivery, wherein the MAMCs release one or more active ingredients in response to mechanical stimuli in a subject's body. The MAMCs provide a platform for stimulating biological regeneration, biological repair, modifying disease, and/or controlling disease in mechanically-loaded musculoskeletal tissues.

16 Claims, 11 Drawing Sheets

(56) References Cited

OTHER PUBLICATIONS

Dubreuil et al., "Elastic Properties of Polyelectrolyte Capsules Studied by Atomic-Force Microscopy and RICM", European Physical Journal E., 12 (2003) pp. 215-221.
Elisseeff et al., "Transdermal Photopolymerization of Poly(Ethylene Oxide)-Based Injectable Hydrogels for Tissue-Engineered Cartilage", Plastic and Reconstructive Surgery, 1999, 104(4), pp. 1014-1022.
Elsner et al., "Mechanical Properties of Freestanding Polyelectrolyte Capsules" A Quantitative Approach Based on Shall Theory, Progr. Colloid Polym. Sci., (2006), 132, pp. 117-123.
Elsner et al., "Tuning of Microcapsules Adhesion of Varying the Capsule-Wall Thickness", Physical Review E., 69, (2004) pp. 013802-1-031802-6.
Engler et al., "Matrix Elasticity Directs Stem Cell Lineage Specification", Cell 126, Aug. 25, 2006, pp. 677-689.
Epstein-Barash H, Orbey G, Polat BE, Ewoldt RH, Feshitan J, Langer R, Borden MA, Kohane DS. A microcomposite hydrogel for repeated on-demand ultrasound-triggered drug delivery. Biomaterials. Jul. 1, 2010 ;31 (19):5208-17. (Year: 2010).
Erickson et al., "Differential Maturation and Structure-Function Relationships in Mesenchymal Stem Cell-and Chondrocyte-Seeded Hydrogels", Tissue Engineering: Part A, vol. 15, No. 5, 2009, pp. 1041-1052.
Erickson et al., "High Mesenchymal Stem Cell Seeding Densities in Hyaluronic Acid Hydrogels Produce Engineered Cartilage with Native Tissue Properties", Acta Biomaterialia, 8, (2002) pp. 3027-3034.
Erickson et al., "Macromer Density Influences Mesenchylmal Stem Cell Chondrogenesis and Maturation in Photocrosslinked Hyaluronic Acid Hydrogels", Osteoarthritis and Cartilage (2009) 17, pp. 1639-1648.
Esser-Kahn et al., "Programmable Microcapsules from Self-immolative Polymers", J. Am. Chem. Soc., 2010, vol. 132, pp. 10266-10268.
Fan et al., "Gelatin Microspheres Containing TGF-B3 Enhance the Chondrogenesis of Mesenchymal Stem Cells in Modified Pellet Culture", Biomacromolecules, 2008, 9, pp. 927-934.
Farrell et al., "Mesenchymal Stem Cells Produce Functional Cartilage Matrix in Three-Dimensional Culture in Regions of Optimal Nutrient Supply", European Cells and Materials, vol. 23, 2012, pp. 425-440.
Farrell et al., "Tunable and Depth-Dependent Mechanics of Agarose/Poly (Ethylene Glycol) Diacrylate Interpenetrating Networks", 5th Orthopaedic Research Society Annual Meeting, 2011 Paper No. 72—1 page.
Fernandes et al., "Quantification of Release from Microcapsules upon Mechanical Deformation with AFM", Soft Matter, 2010, 6, pp. 1879-1883.
Fisher et al., "Maximizing Cartilage Formation and Integration via a Trajectory-Based Tissue Engineering Approach", Biomaterials, Feb. 2014; 35(7); pp. 2140-2148.
Gianola et al., "In Situ Nanomechanical Testing in Focused Ion Beam and Scanning Electron Microscopes", Review of Scientific Instruments, 82, (2011), p. 063901-063901-12.
Glynos et al., "Nanomechanics of Biocompatible Hollow Thin-Shell Polymer Microspheres", Langmuir, 2009, 25(13), pp. 7514-7522.
Glynos et al., "Polymeric Thin Shells: Measurement of Elastic Properties at the Nanometer Scale Using Atomic Force Microscopy", Materials Science and Engineering B, 165, (2009), pp. 231-234.
Griffen et al., "The Role of Mechanical Loading in the Onset and Progression of Osteoarthritis", Exerc. Sport Sci. Rev., vol. 33, No. 4, 2005, pp. 195-200.
Hu et al., "Controlled Rupture of Magnetic Polyelectrolyte Microcapsules for Drug Delivery", Langmuir, 2008, vol. 24, pp. 11811-11818.

Huang et al., "Transient Exposure to Transforming Growth Factor Beta 3 Improves the Mechanical Properties of Mesenchymal Stem Cell-Laden Cartilage Constructs in a Density-Dependent Manner," Tissue Engineering: Part A, vol. 15, No. 11, 2009, pp. 3461-3472.
International Preliminary Report on Patentability for International Application No. PCT/US2016/035220, dated Dec. 5, 2017, 7 pages.
International Search Report and Written Opinion for International Application No. PCT/US2016/035220, dated Aug. 12, 2016, 7 pages.
Kim et al., "Transient Exposure to TGF-B3 Improves the Functional Chondrogenesis of MSC-Laden Hyaluronic Acid Hydrogels", J. Mech. behav. Biomed. Mater., Jul. 11, 2012, pp. 92-101.
Kost et al., "Responsive Polymeric Delivery Systems", Advanced Drug Delivery Reviews, 46 (2001), pp. 125-148.
Kost, Joseph, and Robert Langer. "Responsive polymeric delivery systems." Advanced drug delivery reviews 64 (2012): 327-341. (Year: 2012).
Kurz et al., "Biosynthetic Response and Mechanical Properties of Articular Cartilage After Injurious Compression", Journal of Orthopaedic Research, 19, (2001) pp. 1140-1146.
Lee et al., "Harnessing Interfacial Phenomena to Program the Release Properties of Hollow Microcapsules", Advanced Functional Materials, 2012, vol. 22, pp. 131-138.
Magagnosc et al., "Tunable Tensile Ductility in Metallic Glasses", Scientific Reports, 3: 1096, pp. 1-6, 2013.
Mercade-Prieto et al., "Mechanical Characterization of Microspheres—Capsules, Cells and Beads: A Review", Journal of Microencapsulation, 2011, pp. 1-9.
Mohanraj et al., "A High Throughput Mechanical Screening Device for Cartilage Tissue Engineering", Journal of Biomechanics, 47, (2014) pp. 2130-2136.
Mohanraj et al., "A High Throughput Model of Post-Traumatic Osteoarthritis using Engineered Cartilage Tissue Analogs", Osteoarthritis and Cartilage, 22, (2014) pp. 1282-1290.
Odom et al., "Visual Indication of Mechanical Damage Using Core-Shell Microcapsules", ACS Appl. Mater. Interfaces, 2011, vol. 3, pp. 4547-4551.
Quinn et al., "Matrix and Cell Injury Due to Sub-Impact Loading of Adult Bovine Articular Cartilage Explants: Efforts of Strain Rate and Peak Stress", Journal of Orthopaedic Research, 19, (2001) pp. 242-249.
Rachik et al., "Identification of the Elastic Properties of an Artificial Capsule Membrane with the Compression Test: Effect of Thickness", Journal of Colloid and Interface Science, 301, (2006) pp. 217-226.
Raichur et al., "Adhesion of Polyelectrolyte Microcapsules Through Biotin-Streptavidin Specific Interaction", Biomacromolecules, 2006, 7, pp. 2331-2336.
Rennerfeldt et al., "Tuning Mechanical Performance of Poly(Ethylene Glycol) and Agarose Interpenetrating Network Hydrogels for Cartilage Tissue Engineering," Biomaterials, Nov. 2013: 34(33) pp. 8241-8257.
Saito et al., "Experimental and Computational Characterization Designed and fabricated 50:50 PLGA Porous Scaffolds for Human Trabecular Bone Applications", J. Mater. Sci: Mater. Med. (2010) 21: pp. 2371-2383.
Sander et al., "Nanoparticle-Filled Complex Colloidosomes for Tunable Cargo Release", Langmuir, 2013, vol. 29, pp. 15168-15173.
Shlopov et al., "Differential Patterns of Response to Doxycycline and Transforming Growth Factor B1 in the Down-Regulation of Collagenases in Osteoarthritic and Normal Human Chondrocytes", Arthritis and Rheumatism, vol. 42, No. 4, Apr. 1999, pp. 719-727.
Snejdrova et al., "Pharmaceutically Used Plasticizers", Recent Advances in Used Plasticizers, www.intechopen.com, pp. 45-68, 2012.
Sun, H., "Mechanical Loading, Cartilage Degradation and Arthritis", Annuals of New York Academy of Sciences, 1211 (2010) pp. 37-50.
The Adhesion Society 37th Annual Meeting, Feb. 23-26, 2014, San Diego, CA, 8 pages.

(56) References Cited

OTHER PUBLICATIONS

Thirumalai et al., "Effect of Therapeutic Ultrasound on Acoustically Sensitive Microcapsules", 33rd Annual International Conference of the IEEE EMBS, Boston, MA, Aug. 30-Sep. 3, 2011, pp. 7207-7210.
Tu et al., "Controlling the Stability and Size of Double-Emulsion-Templated Poly (lactic-co-glycolic) Acid Microcapsules", Langmuir, 2012, 28(26), pp. 9944-9952.
White et al., "Autonomic Healing of Polymer Composites", Nature, vol. 409, Feb. 2001, pp. 794-817.
Wilde et al., "Development of a Pressure-Sensitive Glyceryl Tristearate Capsule Filled with a Drug-Containing Hydrogel", International Journal of Pharmaceutics, 461, (2014) pp. 296-300.
Wilde et al., "Development of Pressure-Sensitive Dosage Forms with a Core Liquefying at Body Temperature", European Journal of Pharmaceutics and Biopharmaceutics, vol. 86, 2014, pp. 507-513.
Windberges et al., "Biodegradable Core-Shell Carriers for Simultaneous Encapsulation of Synergistic Actives", J. Am. Chem. Soc., 2013, 135, pp. 7933-7937.
Wu et al., "Self-Healing Polymeric Materials: A Review of Recent Developments", Progress in Polymer Science, 33 (2008) pp. 479-522.
Yang et al., "Core-Shell Structure Microcapsules with dual pH Responsive Drug Release Function", Electrophoresis 2014, 35, pp. 2673-2680.
Zhang et al., "Can Sonication Enhance Release From Liquid-Core Capsules with a Hydrogel Membrane", Journal of Colloid and Interface Science, vol. 368, 2012, pp. 648-654.

\* cited by examiner

Confocal Midsection
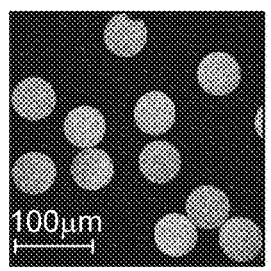
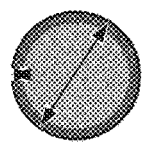
1. thickness
2. outer diameter
FIG. 2a
Fabrication Parameters:
1. PLGA Concentration
2. Fluid Flow Rates
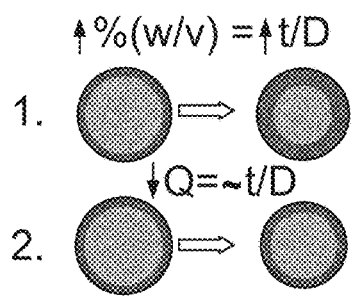
FIG. 2b
| Conc. (%w/v) | Inner (mL/hr) | Middle (mL/hr) | Thickness (μm) | Outer Diameter (μm) | t/D |
|---|---|---|---|---|---|
| 0.9 | 1 | 5 | 0.5 | 76 | 0.006 |
| 1.8 | 2 | 6 | 0.65 | 105 | 0.006 |
| 2.7 | 2 | 6 | 1.01 | 105 | 0.009 |
t = thickness   D = outer diameter
FIG. 2c
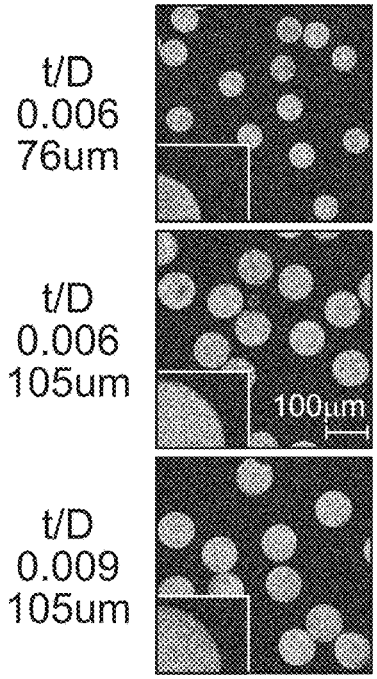
t/D 0.006 76um
t/D 0.006 105um
t/D 0.009 105um
FIG. 2d

1. Seed microcapsules between two glass coverslips (~500 MAMC/test)
2. Apply uniaxial compression at a controlled strain rate (ε=0.5/s) to specified loads (0-1N, 5N '+' control)
3. Image using confocal microscopy to quantity fraction of empty microcapsules based on intensity values

**p<0.01 linear regression slope comparison

***p<0.0001 linear slope regression comparison

- Bulk erosion of PLGA results in the convergence of mechano-activation profiles across t/D ratios

- Continued PLGA degradation results in loss of encapsulated contents and mechanical integrity Matrix Stiffness 1. Embed microcapsules in chemically crosslinked, polyethylene (glycol) diacrylate (PEGDA) hydrogel 2. Apply uniaxial compression on confocal mounted device at increments 5% strain to 20% strain 3. Quantify microcapsule strain in the direction of ($E_{11}$) and perpendicular to ($E_{22}$) compression

MECHANO-SENSITIVE MICROCAPSULES FOR DRUG DELIVERY

CROSS REFERENCE TO RELATED APPLICATIONS

This application is a continuation of currently pending U.S. patent application Ser. No. 15/579,084, filed Dec. 1, 2017, which is a U.S. national phase of International Application No. PCT/US2016/035220, filed Jun. 1, 2016, which claims priority to U.S. Provisional Application No. 62/169,286, filed Jun. 1, 2015. Each of the foregoing applications is incorporated herein by reference in its entirety for any and all purposes.

FIELD OF THE INVENTION

The present invention relates to mechano-sensitive microcapsules for drug delivery, and methods of using the same.

BACKGROUND OF THE INVENTION

In comparison to conventional systemic delivery of therapeutics, controlled drug delivery has several advantages, including localized delivery to specific locations, maintenance of drug concentrations within a desired therapeutic range, and preservation of therapeutic activity for long-term administration. One particularly desirable feature of these systems is self-regulation, wherein physiological feedback actively controls release kinetics. Self-regulating delivery systems often rely on internal triggers for release, such as temperature, pH-sensitivity, enzyme-substrate reactions, or chemical (hydrolysis) reactions. Recent advances in microencapsulation-based ("core-shell") drug delivery systems have used these stimuli-responsive approaches; for example, lipid shells melted at 37° C. have been used to release anti-cancer drugs and shell pH sensitivity has directed antibiotic release in the gastrointestinal tract.

However, there are no controlled delivery vehicles that have been tuned for triggered release in response to mechanical loading, deformation, or stress. Tissues within the body experience mechanical perturbation across multiple force magnitudes and length scales, from mechano-transduction at the cellular level to the dynamics of whole joints. These forces in most tissues are responsible for maintaining tissue integrity, and can initiate degenerative processes at supra-physiologic levels. Thus, there remains a need for drug delivery systems that can be activated in response to mechanical loading, whether it is incurred during rehabilitation, normal activities of daily living, or under conditions likely to produce tissue damage.

SUMMARY OF THE INVENTION

An embodiment of the present invention relates to a method of tuning the rupture profiles of mechanically-activated microcapsules MAMCs to deliver a therapy to a subject. The method includes the steps of identifying one or more rupture profiles that will provide a therapy to a subject based on mechanical loads/stresses/strains (and/or based on the number of loading events/timing of loadings) that are expected to be applied to mechanically-activated microcapsules after they have been administered to the subject, and creating mechanically-activated microcapsules that have said one or more rupture profiles. Each mechanically-activated microcapsule comprises one or more active ingredients encapsulated inside a shell, and the mechanically-activated microcapsules are designed to rupture and release a therapeutically effective amount of said one or more active ingredients when said mechanical loads/stresses/strains are applied to said mechanically-activated microcapsules.

Another embodiment of the present invention relates to a method of using mechanically-activated microcapsules for drug delivery. The method includes delivering the mechanically-activated microcapsules (MAMCs) to a region of a subject's body. The mechanically-activated microcapsules have one or more rupture profiles that enable the mechanically-activated microcapsules to rupture in response to one or more mechanical loads in said region of the subject's body.

Another embodiment of the present invention relates to a composition including a mixture of mechanically-activated microcapsules having a plurality of rupture profiles, e.g., for the purpose of delivering multiple agents suitable for multiple functions and temporal control of their cumulative release.

BRIEF DESCRIPTION OF THE DRAWINGS

FIG. 2A displays a confocal midsection of isolated MAMCs having inner aqueous cores containing fluorescently tagged FITC-dextran and poly-lactic-co-glycolic acid (PLGA) shells tagged with Nile Red according to aspects of the present invention; two parameters of fabrication, MAMC shell thickness and the MAMC outer diameter were investigated.

FIG. 2B illustrates two fabrication parameters, PLGA concentration and fluid flow rates, affecting the MAMC shell thickness to MAMC outer diameter ratio produced by a capillary microfluidic device according to aspects of the present invention.

FIG. 2C displays a table demonstrating the effects of PLGA concentration and fluid flow rates on the characteristics of MAMCs produced using a capillary microfluidics device according to aspects of the present invention.

FIG. 2D displays confocal midsections of isolated MAMCs produced by capillary microfluidics with varied parameters of fabrication according to aspects of the present invention.

DETAILED DESCRIPTION OF THE INVENTION

Figure 1A:
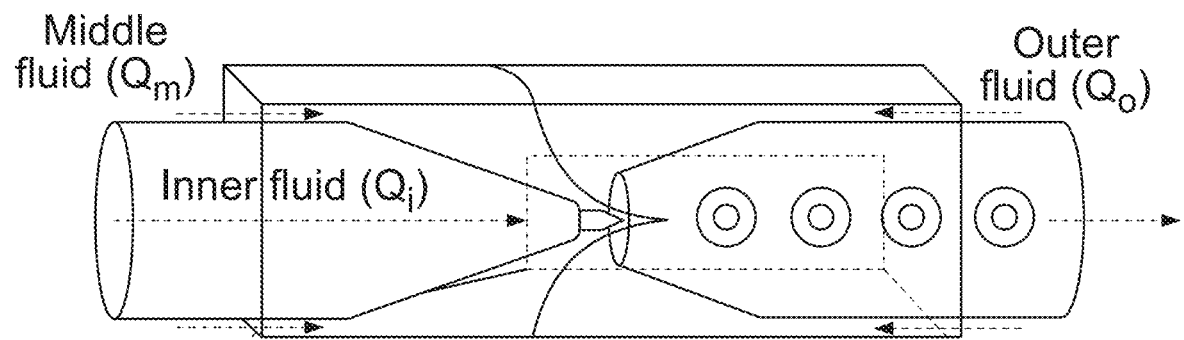
FIG. 1A provides a schematic illustration of an embodiment of a water/oil/water (W/O/W) double emulsion generation from a capillary microfluidic device according to aspects of the present invention.

Embodiments of the present invention relate to mechanically-activated microcapsules (MAMCs) for controlled drug-delivery, wherein the MAMCs release one or more active ingredients in response to mechanical stimuli. According to particular embodiments, the MAMCs of the present invention have release profiles that are tuned to mechanical loading as a mechanism for controlled drug delivery. The MAMCs provide a platform for stimulating biological regeneration and repair in mechanically-loaded tissues of a subject's body (e.g., musculoskeletal tissues, cartilage tissue, etc.).

Previous microcapsules have included various triggered release mechanisms involving chemical or thermal triggers for drug delivery (e.g., pH, heat, osmotic swelling, etc.). However, mechanical feedback has played little role, if any, in release of the active ingredient from these microcapsules. There are currently no microcapsule delivery systems with release mechanisms that are tuned to the endogenous mechanical environment. Embodiments of the MAMCs of the present invention are not designed to rupture (and preferably do not rupture) in response to non-mechanical environmental cues including, without limitation, chemical or thermal triggers, such as a change in pH, or an application of light, heat, osmotic swelling, magnetic field, or ultrasound.

As used herein, mechanically-activated microcapsules (MAMCs) of the present invention (also referred to herein as "microcapsules") comprise hollow microcapsules that encapsulate one or more active ingredients inside a solid shell. According to particular embodiments, the solid shell comprises one or more polymers (i.e., the shell is a "polymer shell"); preferably, the shell comprises poly(lactic-co-glycolic)acid (PLGA) or another FDA-approved material. When pressure/stress/deformation is applied to the MAMCs (e.g., when the MAMCs are compressed), the solid shell begins to deform. When enough pressure (or "load") is applied, the MAMC ruptures, which means that the solid shell breaks and the active ingredient is released from the core of the MAMC into the surrounding environment. Thus, the shell of the microcapsule breaks when a minimum pressure threshold is applied.

The active ingredient(s) are preferably suspended in an aqueous phase that is completely surrounded by the solid shell. As used herein, the "active ingredient" (also referred to as "therapeutic," "active pharmaceutical ingredient," "API," "drug," "biologic," or "active") refers to the pharmaceutically active compound(s) encased inside the core defined by the solid shell. According to particular embodiments, the active ingredient(s) are selected from the group consisting of one or more anti-catabolic compounds that inhibit or arrest cartilage breakdown (e.g., doxycycline), one or more anabolic compounds that encourage repair and regeneration of cartilage (e.g., transforming growth factor beta (TGF-β)), one or more anti-inflammatory compounds, and combinations thereof.

According to preferred embodiments, when MAMCs are delivered to a region of a subject's body (e.g., a joint), the amount of active ingredient(s) released from the MAMCs is a therapeutically effective amount, i.e., the active ingredient(s) that are released from the MAMCs upon rupture of the shell will have a desired therapeutic effect within that region of the subject's body, depending on the nature or severity of that subject's disease or condition; for example, an amount of active ingredient(s) which will cure, prevent, inhibit, or at least partially arrest, delay the onset of or partially prevent a target disease or condition (e.g., tissue damage, tissue breakdown, or tissue inflammation, such as cartilage legions, cartilage injury, or cartilage breakdown within a joint), or one or more symptoms thereof. The embodiment includes delivery to native tissue such as into a joint after injury, or as part of a tissue repair modality (i.e., defect repair with a tissue engineered construct or other cell-based or acellular (non-cell based) therapeutic). Anti-catabolic compounds, anabolic compounds, and anti-inflammatory compounds are well-known, and those of ordinary skill in the art can readily determine appropriate dosages and amounts for use in accordance with the present invention. The terms "subject" and "patient" are used interchangeably herein and refer to a mammalian individual, preferably a human being or animal (e.g. a domesticated pet or thoroughbred horse).

According to particular embodiments, the mechanically-activated microcapsules of the present invention have diameters ranging from about 0.5 µm to about 300 µm, or about 1 µm to about 300 µm, or about 5 µm to about 300 µm, or about 10 µm to about 300 µm, or about 0.5 µm to about 200 µm, or about 1 µm to about 200 µm, or about 5 µm to about 200 µm, or about 10 µm to about 200 µm, or about 0.5 µm to about 100 µm, or about 1 µm to about 100 µm, or about 5 µm to about 100 µm, or about 10 µm to about 100 µm, or about 20 µm to about 300 µm, or about 20 µm to about 200 µm, or about 20 µm to about 100 µm, or about 20 µm to about 75 µm. Preferably, the MAMCs have diameters of about 30 µm to about 70 µm, or about 40 µm to about 60 µm. According to particular embodiments, the shells of the mechanically-activated microcapsules have a thickness of between about 0.05 µm to about 30 µm, or between about 0.05 µm to about 20 µm, or between about 0.05 µm to about 10 µm, or between about 0.05 µm to about 5 µm, or between about 0.1 µm to about 30 µm, or between about 0.1 µm to about 20 µm, or between about 0.1 µm to about 10 µm, or between about 0.1 µm to about 5 µm, or between about 0.25 µm to about 5 µm, or between about 0.25 µm to about 4 µm, or between about 0.25 µm to about 3 µm, or between about 0.5 µm to about 5 µm, or between about 0.5 µm to about 4 µm, or between about 0.5 µm to about 3 µm, or between about 0.5 µm to about 2.5 µm.

Figure 1B:
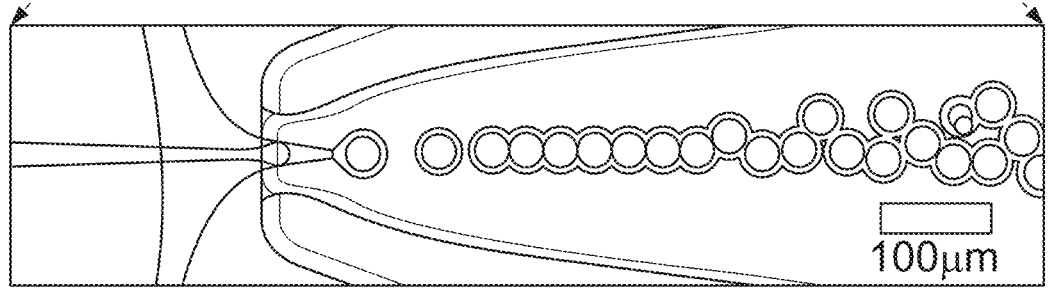
FIG. 1B provides a microscopy image of an embodiment of water/oil/water (W/O/W) double emulsion generation from a capillary microfluidic device according to aspects of the present invention.

According to particular embodiments, the MAMCs of the present invention are made according to the methods described in the 2012 publication by Fuquan Tu and Daeyeon Lee, Controlling the Stability and Size of Double-Emulsion-Templated Poly(lactic-co-glycolic) Acid Microcapsules; Langmuir, 2012; 28(26): pp. 9944-9952, which is incorporated by reference herein, in its entirety and for all purposes. As described therein, microfluidic techniques are used to generate water-in-oil-in-water (W/O/W) double emulsions, which are used to template microcapsule formation. Water-in-oil-in-water (W/O/W) double emulsions are preferably generated using a glass capillary microfluidic device (e.g., FIGS. 1A and 1B). To generate double emulsions, three different fluid phases are injected into the microfluidic device by three syringe pumps with controlled flow rates. According to preferred embodiments, a glass capillary microfluidics device (see, e.g., FIG. 1B) is utilized, wherein the inner phase comprises water and drug(s), the middle phase comprises one or more polymers (e.g., PLGA) and optionally one or more plasticizers and/or one or more stabilizers, and the outer phase comprises one or more stabilizers (e.g., polyvinyl alcohol, surfactant(s), etc.). See FIG. 1C.

Embodiments of the present invention utilize mechanically-loaded environments (e.g., a subject's joint) to trigger and control release of therapeutics. Upon rupture, one or more active ingredients entrapped within the microcapsules can stimulate (i) anabolic processes leading to cell proliferation, differentiation, and/or matrix biosynthesis, or (ii) anti-catabolic processes that inhibit or arrest cartilage breakdown, or (iii) a host of other responses. Because the timing of release is controlled by mechanical load, the release of therapeutics can be "tuned" based on the mechano-sensitivity of the microcapsules. For example, mechanical activation of the microcapsules can be tuned through material selection and microcapsule design, thereby enabling the delivery of encapsulated active ingredients in response to mechanical loading (e.g., walking, running, high-impact sports, etc.). The release properties of the MAMCs under different mechanical loading scenarios can be controlled, for example, by modifying shell thickness-to-radius ratio and shell elasticity/plasticity. Additionally, the composition of the shell, and its degradation in a physiologic setting (e.g., the knee joint) can be further used to define release profiles with expected loading scenarios during rehabilitation and functional tissue formation.

Tuning MAMC rupture characteristics enables the release of active ingredients that stimulate repair and healing in an "on-demand" fashion, thereby providing specific, local, and controlled delivery. For example, MAMCs of the present invention may be embedded within engineered matrices (e.g., engineered cartilage) and may foster regeneration via controlled loading during rehabilitation, or the MAMCs may be designed to actuate in response to injury that occurs during supra-physiologic loads, so as to promote rapid local repair after injury. Embodiments of this technology have the potential to transform the treatment of cartilage lesions and other mechanically-loaded tissues by fostering maturation, preventing degeneration, and/or inducing healing upon tissue damage through the delivery of therapeutics with mechanical perturbation. Thus, the MAMCs can provide a broad range of potential applications in directing regeneration in mechanically-loaded tissues.

A microcapsule's minimum pressure/deformation/stress threshold (i.e., the amount of pressure that is needed to break its shell) varies depending on certain characteristics of the microcapsule (e.g., mechanical properties and structure of the microcapsule shell). In accordance with embodiments of the present invention, characteristics of the microcapsule shell can be "tuned" (i.e., optimized or adjusted) to provide a specific rupture profile based on the mechanical loads that are expected to be applied to the microcapsules after they have been administered to a subject. A "rupture profile" (or "release profile" or "rupture characteristics") refers to the minimum mechanical threshold that must be applied to the microcapsule in order to rupture its shell so that contents encased inside the core of the microcapsule (e.g., one or more APIs) can be released into the surrounding environment. For example, after the microcapsules have been injected or embedded into a subject's joint or other tissue, the drug is released from the microcapsules when the minimum threshold pressure/stress/deformation is realized in the joint, thereby rupturing the microcapsules' shells.

According to particular embodiments, the microcapsules are designed to have specific rupture profiles that enable the shells to rupture and release the active ingredient(s) when subjected to one or more specific mechanical loads within a subject's body (e.g., within a subject's joint). Thus, the microcapsules' shells are designed to rupture when one or more expected mechanical loads are applied to the microcapsules. For example, when microcapsules are administered into a subject's joint, the rupture profiles correlate with the expected mechanical loads that will occur in the joint so that when those mechanical loads are applied to the microcapsules, the microcapsules rupture and release the active ingredients. This allows for controlled drug delivery in response to specific mechanical stimuli or mechanical perturbation. An "expected mechanical load" is the amount of pressure that is expected to be applied in a specific region of a subject's body (e.g., a joint, such a knee joint, elbow joint, shoulder joint, ankle joint, hip joint, or wrist joint) based on mechanics of that region that are known in the art. According to additional embodiments, the MAMCs can be delivered to a region of the body that is not a joint; for example, the MAMCs can be delivered to non-joint tissue (i.e., tissue that is not located within a joint), such as skin, tendon or other tissue, to promote healing or control growth or respond to injury.

The microcapsules may also be designed to break at different loads depending on the type of therapy they are intended to deliver to the subject. For example, the microcapsules may be intended for prophylactic treatment after joint surgery, or for the prevention of post-traumatic osteoarthritis, of for improving cartilage regeneration and repair, or for the delivery of anti-inflammatory therapeutic(s) during high-impact sports. If microcapsules are delivered to a subject's knee, it may be desirable for at least some of the microcapsules to rupture in response to relatively "lower impact" movements (i.e., movements that place relatively lower mechanical loads on the knee), such as walking, and/or for at least some of the microcapsules to rupture in response to "higher impact" movements (i.e., movements that place relatively higher mechanical loads on the knee) such as deep flexion beyond 90° or squatting or movements that are controlled for therapeutic purposes (e.g., during use of post-surgery passive motion devices). The microcapsules may be designed to rupture after a single event (e.g., after exposure to a single mechanical load), or after multiple events over time (e.g., after multiple exposures to mechanical loads). The timing of degradation of the MAMC may also be tuned to elicit the appropriate release profile during rehabilitation or in response to injury.

According to an aspect of the present invention, the mechanically-activated microcapsules that are administered to a subject have one rupture profile, i.e., all of the MAMCs have the same rupture profile or substantially the same rupture profile. According to another aspect of the present invention, the mechanically-activated microcapsules that are administered to a subject have more than one rupture profile, i.e., the MAMCs have varying rupture profiles such that some of the MAMCs have higher minimum pressure thresholds than other MAMCs. This embodiment allows for sequential delivery of one or more therapeutics when microcapsules with different load thresholds are combined together in a region of the subject's body. This embodiment also may allow for continual release as the regenerate tissue that is forming develops increasing mechanical properties, allowing for greater stress transfer to the MAMC as the tissue matures in situ.

According to an embodiment of the present invention, a method of tuning the rupture profiles of mechanically-activated microcapsules to deliver a therapy to a subject comprises identifying one or more "target" rupture profiles that will provide a desired therapy to a subject based on mechanical loads that are expected to be applied to mechanically-activated microcapsules after they have been administered to a region of the subject's body (e.g., by determining or estimating the mechanical load to which the region of the subject's body is subjected), and creating mechanically-activated microcapsules that have the one or more target rupture profiles, wherein the mechanically-activated microcapsules are designed to rupture and release a therapeutically effective amount of one or more active ingredients (i.e., an amount effective to provide the desired therapy) when the expected mechanical load(s) are applied to the mechanically-activated microcapsules. The MAMCs having the appropriately tuned rupture profiles can then be delivered to the desired region of the subject's body for the therapy.

According to particular embodiments, mechanically-activated microcapsules having the target rupture profile(s) can be created by providing a suitable shell thickness or mechanical property of the shell. For example, MAMCs with a relatively smaller shell thickness (e.g., 0.5 microns) have a lower minimum pressure threshold that must be applied to rupture the shell, compared to MAMCs with a relatively larger shell thickness (e.g., 2.5 microns), which will have a higher minimum pressure threshold that must be applied to rupture the shell (assuming all the other characteristics of the MAMCs are the same). Shell thickness can be modified, for example, by (i) changing the flow rate of at least one fluid injected into the microfluidic device selected from middle and inner fluids, and/or (ii) changing the ratio of flow rates of the middle fluid and inner fluid injected into the microfluidic device, and/or (iii) changing the concentration of PLGA in the middle phase.

According to additional embodiments, the rupture profile(s) can be controlled by modifying mechanical properties of the mechanically-activated microcapsule shells, for example, by modifying the stiffness or ductility of the shells. Stiffness and or ductility and/or durability may be modified by modifying the concentration of one or more plasticizers in the shells (e.g., by adding one or more plasticizers to the shell compositions). The one or more plasticizers may be selected from the group consisting of diethyl phthalate, tributyl acetyl citrate, vitamins, vegetable oils and a combination thereof. According to particular embodiments, the higher the concentration of plasticizer(s) in the shell, the higher the minimum pressure threshold that must be applied to rupture the shell.

According to an embodiment of the present invention, a method of using mechanically-activated microcapsules for drug delivery comprises delivering mechanically-activated microcapsules (MAMCs) to a region of a subject's body, wherein the mechanically-activated microcapsules have one or more rupture profiles that enable the mechanically-activated microcapsules to rupture in response to one or more mechanical loads in said region of the subject's body. Preferably, the MAMCs are delivered to a region of a subject's body that is a joint, most preferably an articulated joint (e.g., a knee joint, elbow joint, shoulder joint, wrist joint, ankle joint or hip joint). Alternatively, the MAMCs can be delivered to a "non-joint" region of the subject's body (e.g., skin). The MACMs are preferably designed to provide a localized therapeutic effect to the region of the subject's body in which they are delivered (as opposed to a systemic therapeutic effect).

According to one aspect of the invention, mechanically-activated microcapsules are injected or otherwise administered into a subject's joint. For example, the microcapsules are injected into tissue that is within or surrounding the joint (e.g., the microcapsules are injected into musculoskeletal tissue or cartilage located in or around the joint). According to another aspect of the invention, the mechanically-activated microcapsules are embedded within a matrix material (e.g., gel and/or engineered tissue for cartilage repair/replacement) and the matrix material is delivered into a subject's joint. For example, the MAMCs may be embedded in a polymeric material that has a stiffness comparable to native cartilage; the polymeric material may comprise poly (ethylene glycol) diacrylate (PEGDA), methacrylated hyaluronic acid (HA), or one or more other polymers. The matrix material can be injected into a joint or implanted surgically into a joint.

According to particular embodiments, the MAMCs that are delivered to a region of the subject's body have a plurality of different rupture profiles (e.g., at least two different minimum load thresholds). For example, the MAMCs have more than one shell thickness (e.g., selected from 0.5, 1, 1.5, 2, and 2.5 microns) and/or one or more shell compositions (e.g., selected from PLGA without any plasticizers, PLGA with one or more plasticizers, and PLGA with varying concentrations of plasticizer). The MAMCs having a plurality of different rupture profiles (e.g., two or more rupture profiles) may be embedded into a matrix material that is implanted into a joint. A mixture of MAMCs with varying rupture profiles may be desirable for rehabilitation regimens in which the active ingredients are released from embedded microcapsules as the implanted matrix material degrades over time. The method may further comprise a step of selecting the mechanically-activated microcapsules according to their rupture profile(s).

According to embodiments of the invention in which the MAMCs are embedded within a matrix (e.g., a polymer material), the rupture profile of the MAMCs can be adjusted by modifying the physical properties of the matrix, thereby modifying the adhesion of the MAMCs to the matrix. Strong interfacial adhesion between microcapsules and the matrix is known to effect capsule rupture. Thus, modifying the nature of adhesive interaction (e.g., electrostatic vs. protein-ligand interactions) can influence rupture. Also, modifying the ratio of the elastic modulus of embedding matrix to that of shell may determine whether crack propagation occurs through or deflects around microcapsules. During fabrication of MAMCs, adhesion properties can be tuned; for example, by covalently bonding microcapsules to the hydrogel upon photopolymerization. Alternatively, adhesion can be controlled using electrostatic interactions where either the shell or hydrogel is modified with a surface charge. Thus, there are several ways in which the MAMCs can be designed to rupture in response to the mechanics or degeneration of a matrix in which they are embedded.

According to an embodiment of the present invention, a composition comprises a mixture of MAMCs having a plurality of rupture profiles. For example, the MAMCs in the composition have more than one shell thickness (e.g., selected from 0.5, 1, 1.5, 2, and 2.5 microns) and/or one or more shell composition (e.g., selected from PLGA without any plasticizers, PLGA with one or more plasticizers, and PLGA with varying concentrations of plasticizer). The composition may further comprise a pharmaceutically acceptable carrier (i.e., an excipient, diluent, preservative, solubilizer, emulsifier, adjuvant, and/or vehicle with which the MAMCs are administered). For example, such carriers may comprise a liquid, such as water, saline solution, dextrose solution, fibrin gel, or glycerol solution. The composition may also comprise one or more excipients (e.g., wetting or emulsifying agents; pH buffering agents such as acetates, citrates or phosphates; antibacterial agents such as benzyl alcohol or methyl parabens; antioxidants such as ascorbic acid or sodium bisulfite; chelating agents such as EDTA, etc.). According to particular embodiments, the composition is embedded within a matrix (e.g., a hydrogel or other polymeric material that does or does not deliver cells and that has a stiffness similar to that of native cartilage or that can mature to that point via cell-mediated matrix deposition).

According to particular embodiments, a method of making a composition of the present invention comprises mixing the components of the composition together (e.g., mixing the MAMCs having a plurality of rupture profiles with an optional pharmaceutical carrier and one or more optional excipients). The method may further comprise embedding the composition within a matrix material. The compositions of the present invention can be administered to a subject in accordance with any of the methods described herein; for example, by injection into a subject's joint.

As described herein, mechanically activatable microcapsules can be used to controllably deliver bioactive factors upon mechanical stimulation. This has specific applications in cartilage repair, where rehabilitation regimens might be tuned to slowly instigate release of factors from embedded microcapsules as the implanted tissue matures. In addition, this technology can be applied to instances of cartilage injury due to trauma. Inclusion of MAMCs that release in response to injury may be used to protect regenerate tissue and improve durability of repair in populations at risk for re-injury. More generally, this technology may find broad application in a variety of mechanically loaded musculoskeletal regeneration and repair applications.

The embodiments of the invention are described above using the term "comprising" and variations thereof. However, it is the intent of the inventors that the term "comprising" may be substituted in any of the embodiments described herein with "consisting of" and "consisting essentially of" without departing from the scope of the invention. Unless specified otherwise, all values provided herein include up to and including the starting points and end points given.

The following examples further illustrate embodiments of the invention and are to be construed as illustrative and not in limitation thereof.

EXAMPLES

Example 1. Fabrication of Mechanically-Activated Microcapsules (MAMCs) and Determination of how Variations in Fabrication Parameters Influence the Structure-Release Properties of Individual MAMCs In this first formulation, microcapsules were 100 μm in diameter with a shell thickness of 1 μm, and the shell was doped with a fluorescent dye (Nile Red) to enable visualization (FIG. 2A). To demonstrate mechano-activation, a single layer of MAMCs was subjected to increasing levels of load using a mechanical testing device (FIG. 2A). Results showed graded microcapsule rupture and release of FITC-dextran with increasing load (FIG. 2B). Intact microcapsules served as negative controls and sheared microcapsules (completely devoid of FITC-dextran due to complete rupture) served as positive controls. Fluorescent intensity of the buffer solution (indicating FITC-dextran release) correlated with load. Similar activity assays can be used to directly measure cumulative drug release for a given application.

Figure 1C:
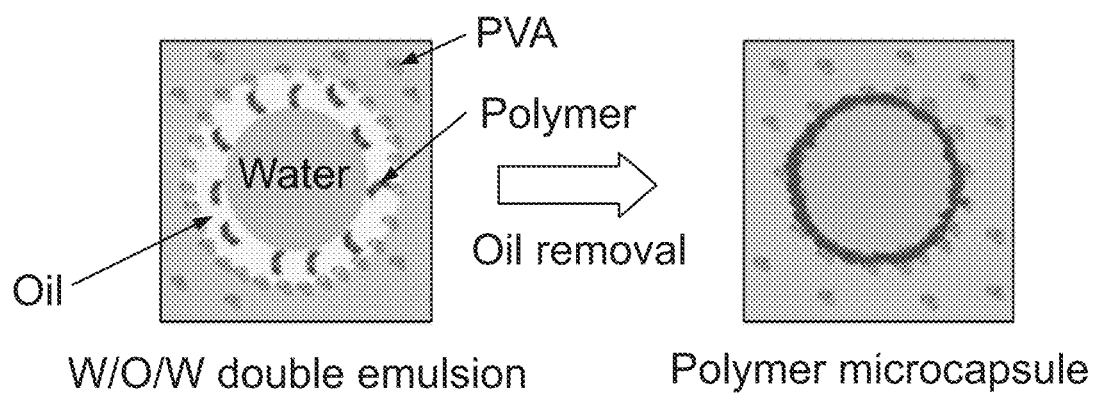
FIG. 1C provides a schematic illustration showing an embodiment of the formation of a polymer microcapsule (MAMC) from a W/O/W double emulsion according to aspects of the present invention.

In this example, a model microcapsule system comprised a poly(lactic-co-glycolic) acid (PLGA) copolymer shell with a soluble fluorescently-tagged molecule (FITC-dextran) encapsulated within an aqueous core. The MAMCs were fabricated using a glass-capillary microfluidic system (FIGS. 1A and 1B) to produce a highly monodisperse water-in-oil-in-water (W/O/W) emulsion with approximately 100% encapsulation efficiency (FIG. 1C). Physical characteristics of the MAMCs were modified, including shell thickness-to-outer diameter ratio, to define thresholds at which different MAMCs fail and release entrapped biomolecules. A systematic approach can be used to develop a suite of MAMCs with different properties, and their elastic, plastic, and failure behaviors may be assessed using quantitative micromechanical analysis tools (including atomic force microscopy (AFM) and reflective interference contrast microscopy). This example may further define the mechanical thresholds that instigate microcapsule rupture, and may further establish the parameter space under which these MAMCs are operative.

1. Microcapsule Fabrication.

As described above, a glass-capillary microfluidic device (FIGS. 1A and 1B) were used to fabricate MAMCs with differing physical attributes. Double emulsions were formed having inner aqueous phases containing a "model" drug (e.g., FITC-dextran, which is a fluorescently tagged molecule). The aqueous solution including the model drug was, in this instance, saline. The middle fluid phase of the double emulsion, or the oil phase, included a suitable polymer for producing the shell of the MAMCs (e.g., poly-lactic-co-glycolic acid or PLGA). The polymer may be biodegradable and biocompatible. The oil phase including the polymer was, in this instance, chloroform. The oil phase was also doped with a dye compound (e.g., Nile Red) to visualize the resulting MAMC shells. The outer fluid phase was also an aqueous fluid to result in a W/O/W double emulsion (FIG. 1C). The final result of the fabrication was MAMCs having Nile Red-dyed PLGA shells encapsulating fluorescent FITC-Dextran. FIG. 2A displays a confocal midsection of MAMCs produced according to this process. The inventors hypothesized that the ratio (t/D) between two parameters of fabrication, the thickness of the microcapsule shell and the outer diameter of the microcapsule, would control release thresholds and mechano-activation of the microcapsules. See FIG. 2A.

MAMC Shell Thickness.

Shell thickness can be varied by altering the polymer (e.g., PLGA) concentration in the oil phase of the double emulsion, or by changing the ratio of flow rates of the middle oil phase (e.g., containing PLGA) and inner aqueous phase (e.g., containing model drug FITC-dextran). See FIG. 2B. Increases in the polymer (e.g., PLGA) concentration increased the shell thickness, which increased the shell thickness to outer microcapsule diameter ratio (t/D). Decreasing the ratio of middle oil phase:inner aqueous phase flow rates results in decreasing shell thickness; however, there is often a lower limit for shell thickness due to susceptibility to rupture in the high shear microfluidic environment, depending on the radius of the microcapsule. Also, decreases in both flow rates resulted in thinner shell walls and smaller microcapsule outer diameter. See FIGS. 2C and 2D, which demonstrate the effects of changing polymer concentration and flow rates on the t/D ratio. Alternatively, changing the concentration of PLGA in the middle phase may also affect shell thickness. Practical considerations for optimizing shell thickness may include sensitivity to handling as well as stiffness and proclivity to fracture under defined loads. Target shell thicknesses may preferably range from about 0.5 µm to about 2.5 µm.

Mechano-Activation of MAMCs with Different Dimensions.

The inventors hypothesized that the t/D ratios and outer diameter fabrication parameters of the microcapsules affected the mechano-activation of the microcapsules. A series of quantitative assays were performed to evaluate MAMC properties as a function of fabrication parameters.

Atomic force microscopy (AFM) is a powerful method for characterizing elastic and plastic deformation of single microcapsules. For uniform compression, a tipless cantilever (simulating a parallel plate) is used to load and unload MAMCs at a constant displacement rate to generate force vs. displacement curves. The linear region of these curves can be used to estimate elastic properties of the shell, namely the shell stiffness (slope) and the Young's modulus using an analytical solution. Thin shell theory holds if: (1) the ratio of shell thickness to radius is less than 1/20, (2) the shell material is linearly elastic, homogeneous, and isotropic, (3) deformation is small (on the order of shell thickness), and (4) shell thickness is constant. For large deformations in the non-linear region of the force-deformation curve, onset of permanent plastic deformations can be quantified by measuring instability (microcapsule buckling) and hysteresis. With repeated loading-unloading cycles (simulating fatigue), instabilities may appear as inflection points at lower forces and deformations. In addition, hysteresis may increase, such that the traces no longer align. To extract intrinsic properties such as yield and strain at rupture, finite element models may need to simulate large deformations using 3D constitutive laws. Since thin shell theory holds regardless of length scale, several trends have been noted for predicting elastic and plastic behaviors of microcapsules. (1) As diameter of the microsphere increases, effective shell modulus decreases (approaches bulk properties) and as shell thickness decreases, effective shell modulus increases and is higher than the bulk polymer modulus. (2) For large deformations, with increasing cantilever stiffness more instabilities appear in smaller diameter microcapsules due to higher forces. The probability of instability also increases with more compliant shells. During characterization of MAMCs, single cycle and repeated cyclic compression by AFM will be used (coupled with measurement of fluorescent intensity of the microcapsule contents) to establish deformation magnitude and cycle number thresholds for failure for different MAMC formulations.

Figure 3A:
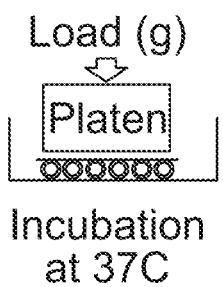
FIG. 3A illustrates a methodology to characterize mechano-activation and load sensitivity using parallel plate compression in which MAMCs are seeded between two cover slips and compressed at a controlled increasing strain rate at a constant temperature of 37° C., according to aspects of the present invention.
Figure 3B:
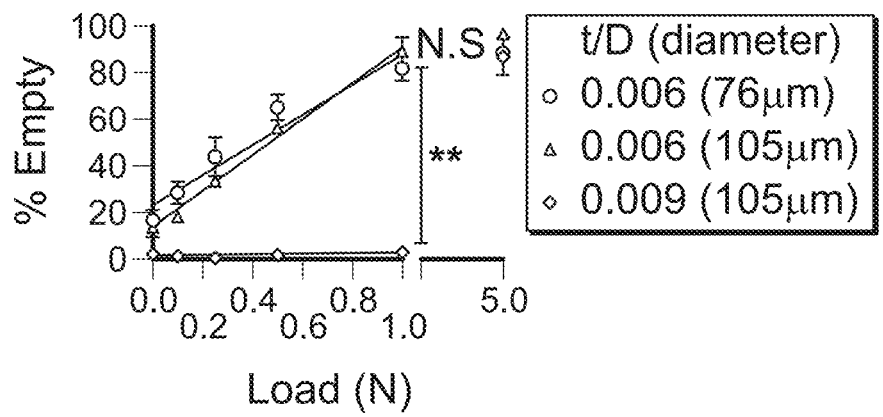
FIG. 3B illustrates mechano-activation and durability to applied loads for three MAMC groups having different shell thickness to MAMC outer diameter ratios or different MAMC outer diameters according to aspects of the present invention.
Figure 3C:
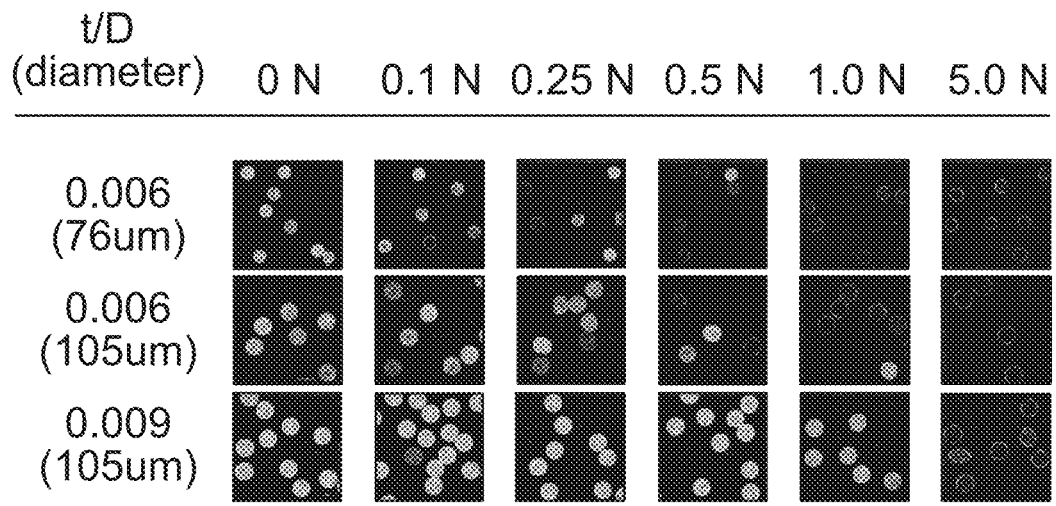
FIG. 3C displays confocal microscopy images of MAMCs having different shell thickness to MAMC outer diameter ratios or different MAMC outer diameters after applying increasing strain rates according to aspects of the present invention.

Another quantitative assay for characterizing mechano-activation and load-sensitivity in MAMCs having different fabrication characteristics was carried out using parallel plate compression in which MAMCs were seeded between two glass coverslips (FIG. 3A). The MAMCs were uniaxially compressed at a controlled strain rate to specified loads ranging from 0 to 1 newton (N), with 5N serving as a positive, completely ruptured control. The MAMCs were then collected and imaged using confocal microscopy to quantify the fraction of empty microcapsules (FIG. 3C). Increasing the shell thickness of the MAMCs resulted in increasing insensitivity to load within the same load range (as demonstrated by MAMCs of the same diameter, but different t/D ratios). See FIGS. 3B and 3C. However, the groups of MAMCs having the same t/D ratios, regardless of outer MAMC diameters, demonstrated the same mechano-sensitivity as load (N) increased. See FIGS. 3B and 3C. The group of MAMCs having a t/D ratio of 0.009 (as a result of a thicker outer shell) demonstrated very little mechano-sensitivity from 0 to 1 newton. See FIGS. 3B and 3C. Thus, the inventors have discovered that MAMC release profiles are highly dependent on the t/D ratios, where the ratio and not only the shell thickness influences crack propensity and durability to an applied load.

Mechanical properties of MAMC shell. In addition to microcapsule dimensions, the inventors hypothesized that the mechanical properties of the shell material influence rupture. Rupture of single MAMCs may occur either (1) within or close to the elastic regime (fractional deformation at rupture <0.2), or (2) after extensive plastic deformation, depending on the brittle or ductile nature of the polymer. Pure PLGA has an elastic modulus of about 2-3 GPa. The PLGA shell can be doped with a biocompatible, hydrophobic plasticizer (e.g., diethyl phthalate, tributyl acetyl citrate) to reduce the shell stiffness. This low water-soluble plasticizer, at appropriate concentrations (<10% w/v), will increase plasticity of the shell, but still allow for rupture. In a single cycle loading scenario (e.g., impact injury), brittle failure would be preferable for immediate release, but for a dynamic (cyclic) loading scenario (e.g., during rehabilitation of a maturing engineered cartilage defect, over which cycles of loaded and unloaded periods may occur, simulating fatigue), plasticity of the microcapsule will be particularly important for regulating delayed onset of rupture. Different ranges of plasticizer concentrations may manipulate MAMC elastic and plastic deformation characteristics to tune release; for example, plasticizer concentrations may be varied between about 0.01 wt % and about 30 wt % plasticizer relative to the total shell composition to change release characteristics.

Reflective Interference Contrast Microscopy (RICM) is used to measure the adhesion area and energy of microcapsules on a specific substrate (to simulate matrix-microcapsule interactions). Microcapsules are illuminated with monochromatic light in a reflection geometry and the interference pattern yields information on the local distance between the capsule wall and glass surface (post-processing image analysis of adhesion area). Adhesion is influenced by the microcapsule-substrate interaction and by the properties and geometry of the shell, where softer microcapsules with a low thickness-to-radius ratio have higher adhesion energy. Using the above techniques, a range of shell thicknesses and polymer compositions can be assayed to determine how these parameters influence MAMC deformation and rupture under static and dynamic load.

The inventors' discoveries regarding the fabrication parameters of MAMCs and shell mechanical properties allow for a suite of microcapsules to be developed whose mechano-activation is defined by the mechanical properties and dimensions of the shell and overall microcapsule. Different formulations may be developed based on different MAMC characteristics, for example, variations in shell thicknesses (e.g., 0.5, 1, 1.5, 2, and 2.5 microns), outer diameters of the microcapsules, and material properties of the shell (e.g., PLGA, PLGA with low plasticizer, PLGA with high plasticizer). Thus, activation of these MAMCs may be achieved across a range of loads/deformations and number of compression cycles. This may allow for tuning of release in response to forces and deformations experienced by the MAMCs In the model gel systems and in living constructs exposed to physiologic and pathophysiologic loading.

Example 2

Figure 4A:
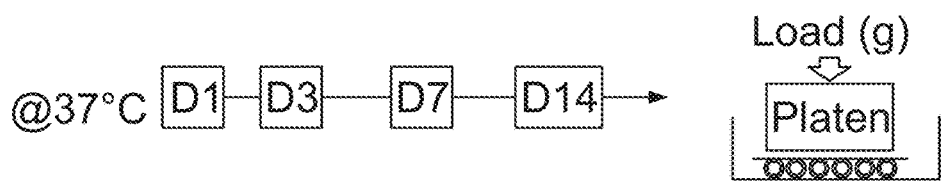
FIG. 4A depicts a schematic of a methodology to characterize degradation and durability of MAMCs having PLGA shells over 14 days at constant physiologic temperature (37° C.), according to aspects of the present invention.
Figure 4B:
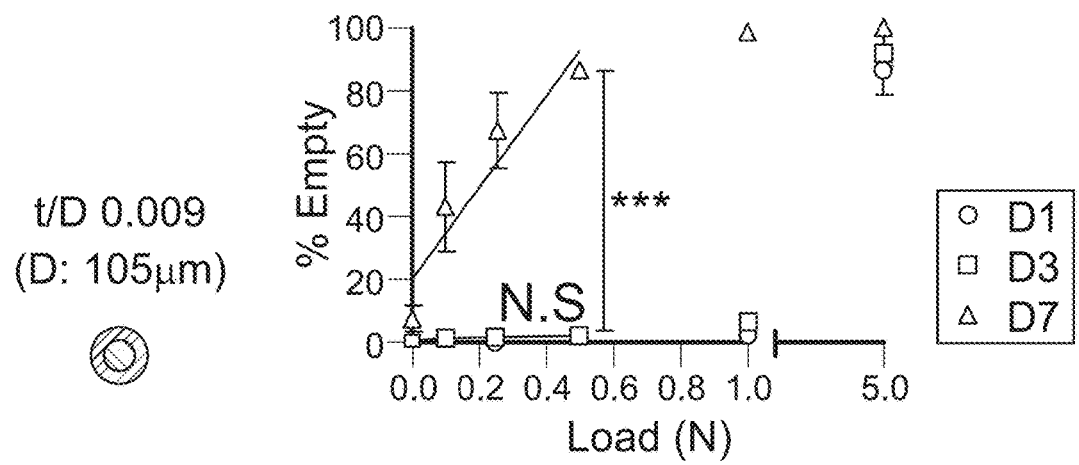
FIG. 4B illustrates mechano-activation of MAMCs having PLGA shells incubated at a constant physiologic temperature of 37° C. and subjected to different loads over 7 days, according to aspects of the present invention.
Figure 4C:
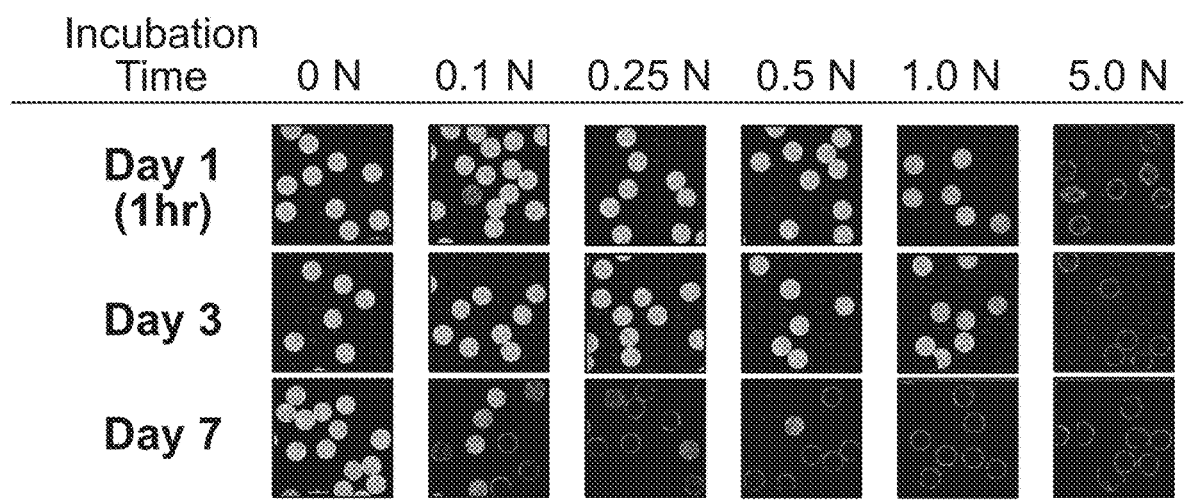
FIG. 4C displays confocal microscopy images of MAMCs having PLGA shells subjected to different loads after incubation at 37° C. at days 1, 3, and 7, according to aspects of the present invention.

In this example, the effects of polymer degradation of MAMC shells at physiologic temperature (37° C.) on mechano-activation were explored. Using the same parallel plate technique as described above in Example 1, MAMCs were tracked over a period of 14 days at different loads between 0 and 1 Newton, with 5 Newtons as a completely ruptured control. See FIGS. 4A and 4B. The group of MAMCs demonstrating the highest resistance to load from Example 1 (t/D of 0.009 and outer diameter of 105 μm) was used. Within the first three days of incubation at 37° C., the mechano-sensitivity of the MAMCs was unaffected. However, by day 7, the microcapsule mechanical release profile is significantly affected by application of load. See FIGS. 4B and 4C. This demonstrates that degradation of the polymer shell has a marked effect on mechanically controlled rupture and release of the MAMCs.

Figure 5A:
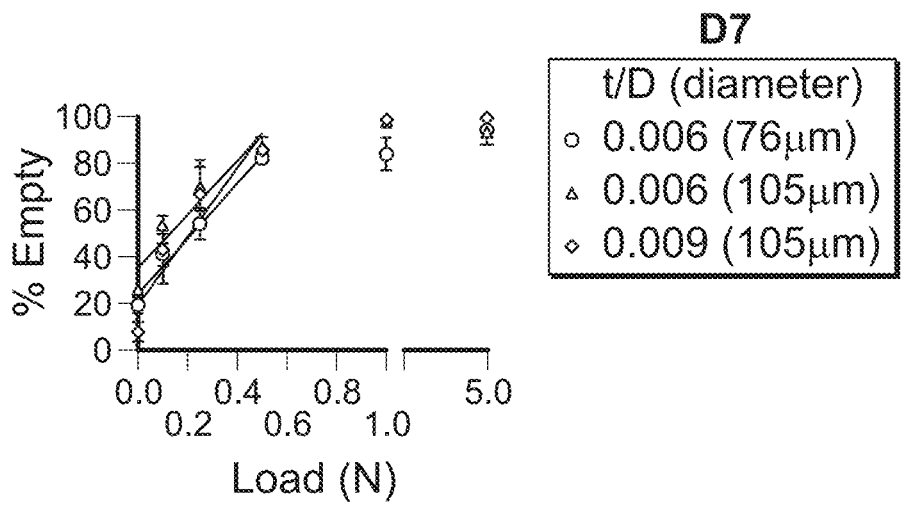
FIG. 5A illustrates mechano-activation profiles of three different groups of MAMCs after seven days of incubation at 37° C., according to aspects of the present invention.
Figure 5B:
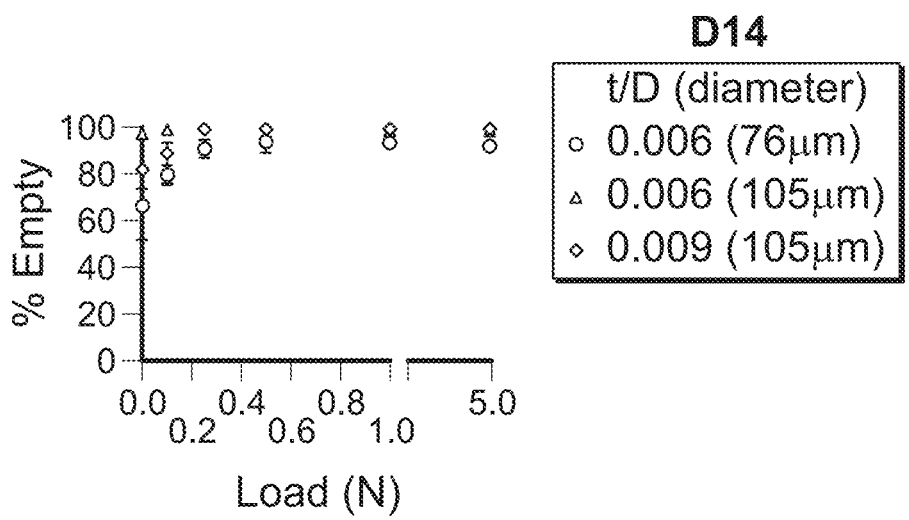
FIG. 5B illustrates mechano-activation profiles of three different groups of MAMCs after fourteen days of incubation at 37° C., according to aspects of the present invention.

A similar methodology was carried out over 14 days using three different classes of MAMCs. See FIGS. 5A and 5B. The sum effect of degradation demonstrated that the bulk erosion of shell polymer (e.g., PLGA) resulted in the convergence of mechano-activation profiles across a range of t/D ratios after seven days of incubation at 37° C. (FIG. 5A), but by day 14, even microcapsules under zero load had lost their encapsulated contents and mechanical integrity as quantified by the empty fraction (FIG. 5B). By day 14, all microcapsules subjected to load completely fractured.

Figure 6:
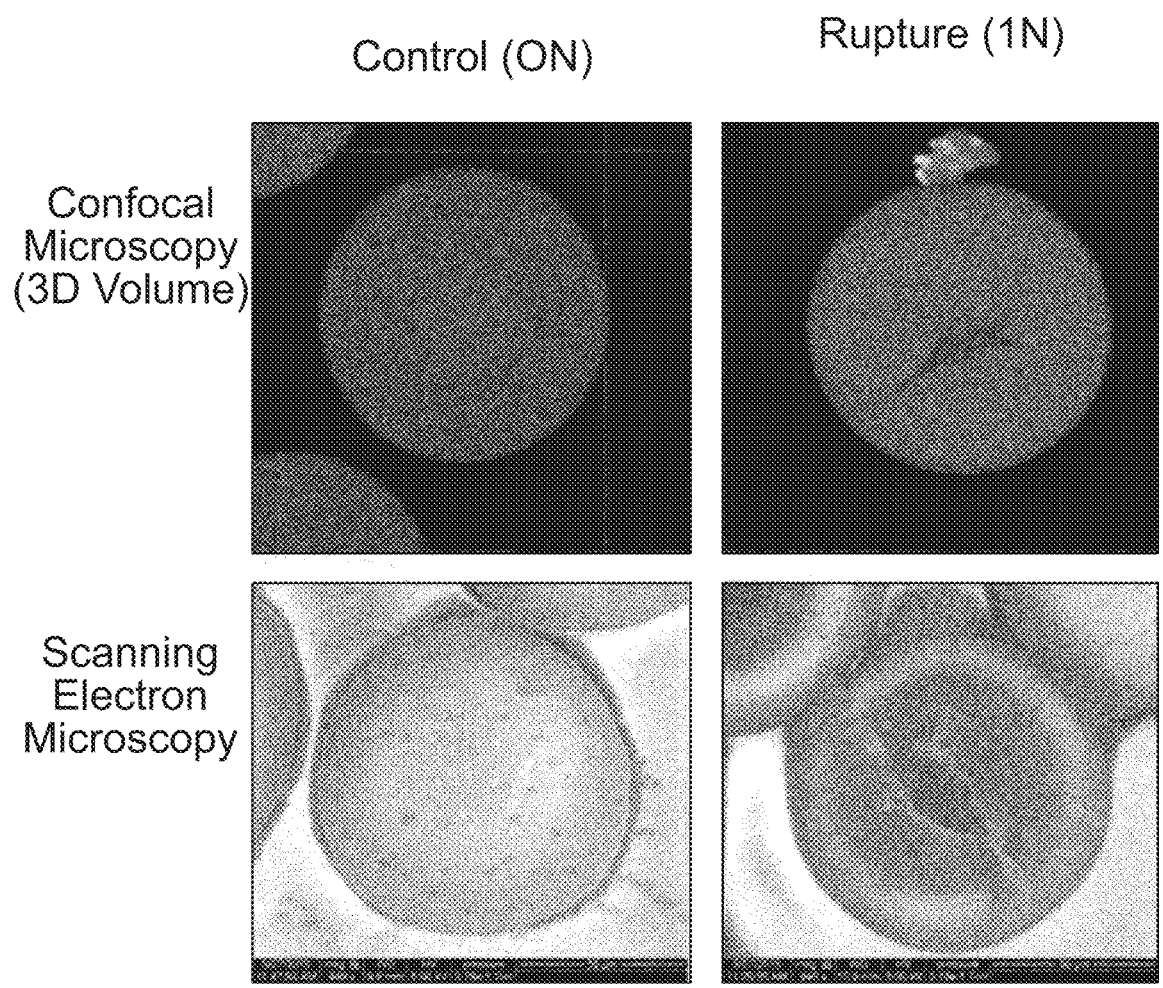
FIG. 6 displays confocal microscopy and scanning electron microscropy images of MAMCs after seven days of incubation at 37° C., according to aspects of the present invention.

FIG. 6 depicts reconstruction of the volume (confocal microscopy images) and the morphology (scanning electron microscopy images) of MAMCs having PLGA shells and core FITC-dextran contents, after seven days of incubation at 37° C. The images demonstrate the rupture mechanism in three dimensions. Control samples (under ON load) maintain their core FITC-dextran contents, but the same MAMCs demonstrate loss of fluorescence under 1N load. Differences in morphology were confirmed using scanning electron microscopy, with MAMCs shown to be ruptured across the midplane of the sphere under 1N load.

Example 3. Microcapsule Mechano-Activation in 3D Hydrogels

Figures 7A, 7B, 7C, 7D:
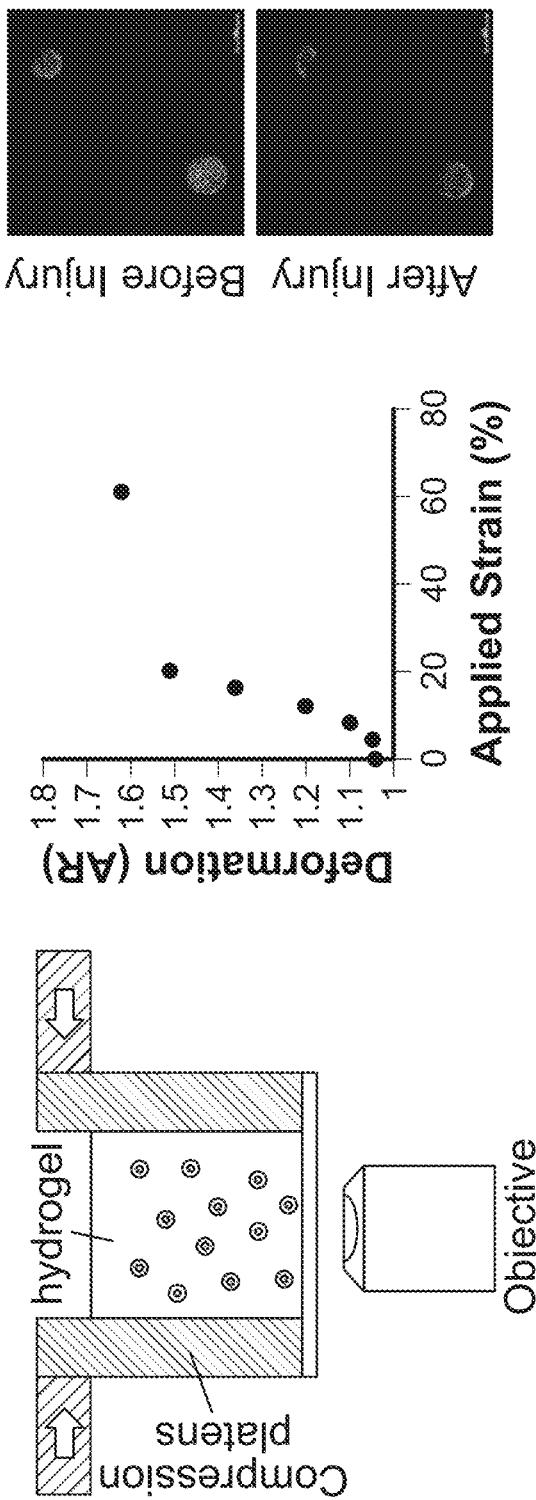
FIG. 7A illustrates a device for imaging mechano-activation and deformation of MAMCs in a three-dimensional (3D) gel matrix, according to aspects of the present invention.
FIG. 7B illustrates quantification of deformation, or aspect ratio (AR), of MAMCs in 3D gel matrix, as a function of applied strain, according to aspects of the present invention.
FIG. 7C depicts microscopy images of MAMCs in 3D gel matrix according to aspects of the present invention before and after injurious compression.
FIG. 7D depicts microscopy images of MAMC deformation of MAMCs in 3D gel matrix during stepwise deformation of the gel according to aspects of the present invention.
Figure 9A:
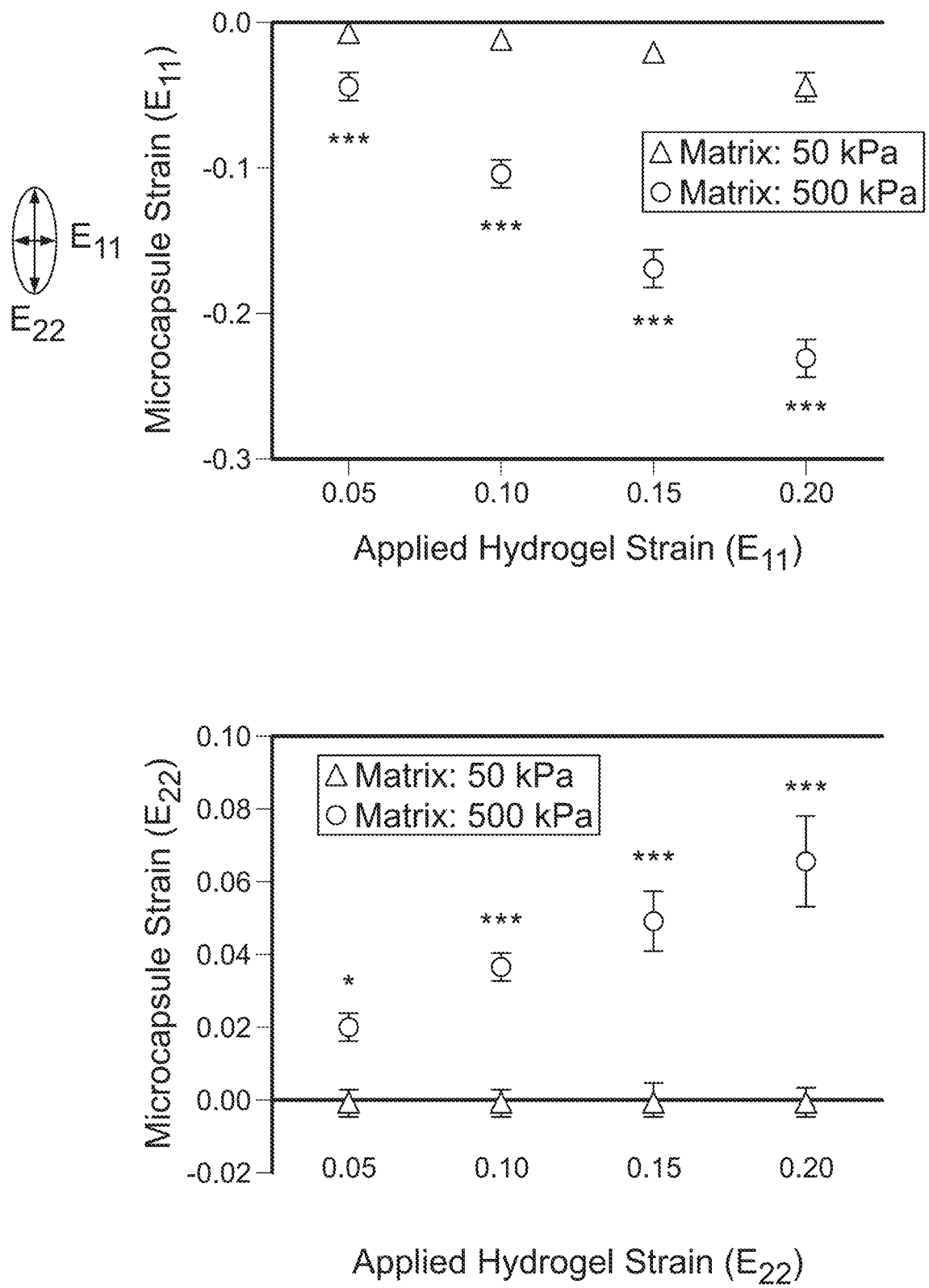
FIG. 9A illustrates strain and deformation of MAMCs in two different gel matrices having different stiffness levels (50 kPa and 500 kPa), according to aspects of the present invention.
Figure 9B:
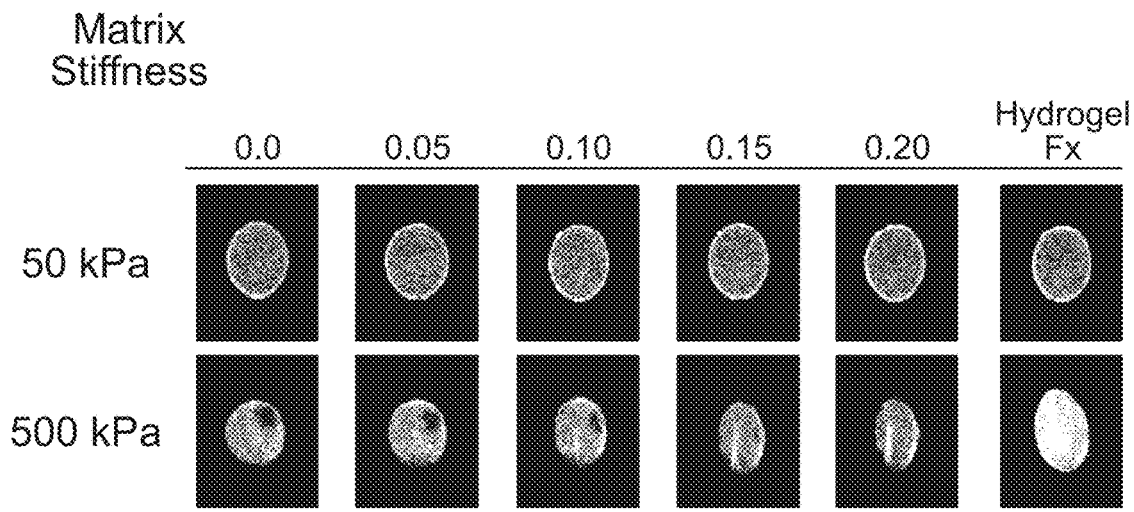
FIG. 9B depicts confocal microscopy images of MAMCs demonstrating levels of deformation in two different gel matrices having different stiffness levels (50 kPa and 500 kPa), according to aspects of the present invention.
Figure 9C:
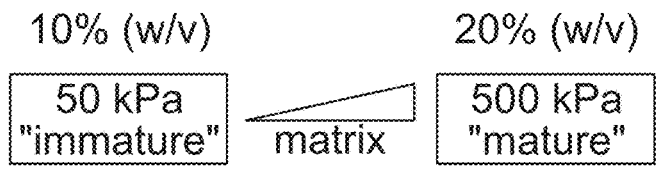
FIG. 9C illustrates a methodology to characterize and quantify mechano-activation and strain on MAMCs embedded in PEGDA gel matrix, according to aspects of the present invention.
Figure 9C:
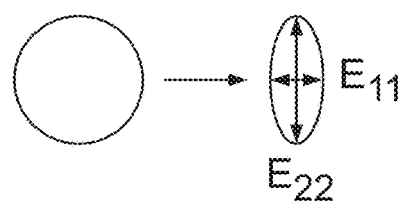

In this example, the deformation of MAMCs embedded in 3D matrices (analogous to engineered constructs mimicking cartilage) was explored. To validate mechano-activation in a three-dimensional (3D) construct, microcapsules were embedded in 30% photo-crosslinked poly(ethylene glycol) diacrylate (PEGDA). See FIG. 9C. This hydrogel was chosen because its stiffness is comparable to native cartilage and matured engineered cartilage. Using a custom micromechanical compression device mounted on a confocal microscope (FIG. 7A), MAMC-laden hydrogels were compressed in unconfined compression (0-20% strain, steps of 4%, followed by compression until hydrogel failure). MAMCs deformed with increasing hydrogel compression, becoming ellipsoid at 20% strain and visibly rupturing at 60% strain (FIGS. 7B and 7D). FIG. 7B depicts the performance of MAMCs embedded in 3D gel matrix, as a function of applied strain; FIG. 7B further demonstrates how the surrounding matrix stiffness controls when and whether a MAMC will deform and rupture. To test for rupture under pathophysiologic loading, injurious compression (20% strain at 50% strain/sec) was applied to fracture the hydrogel. Here, MAMCs buckled and released their contents (FIG. 7C).

In the following examples, further analysis of MAMC deformation in 3D matrices and the mode of rupture (brittle vs. ductile failure) as a function of fabrication parameters defines mechanical thresholds and enables tunable release.

Example 4. Measuring and Modeling Rupture and Biofactor Release from MAMCs Embedded in 3D Matrices as a Function of Matrix Stiffness, Matrix-Capsule Adhesion, and Loading In this example, microcapsule properties (e.g., the ratio of shell elasticity to matrix elasticity, shell thickness, and adhesion to local matrix) are studied with respect to how these properties dictate failure and release characteristics with loading when MAMCs are embedded in 3D matrices of varying properties. Using a novel micromechanical test system, deformation and rupture of MAMCs embedded in 3D matrices (photo-crosslinked hydrogels) of varying elasticity are evaluated as a function of loading conditions, and the release of encapsulated fluorescent molecules will be tracked by confocal microscopy to determine mechanical thresholds for each microcapsule formulation. Finite element (FE) analysis are used to model microcapsule mechanical response, and rupture and release will be predicted over a range of microcapsule fabrication and 3D matrix properties. Microcapsule-gel composites are evaluated through the following assays.

Figure 8:
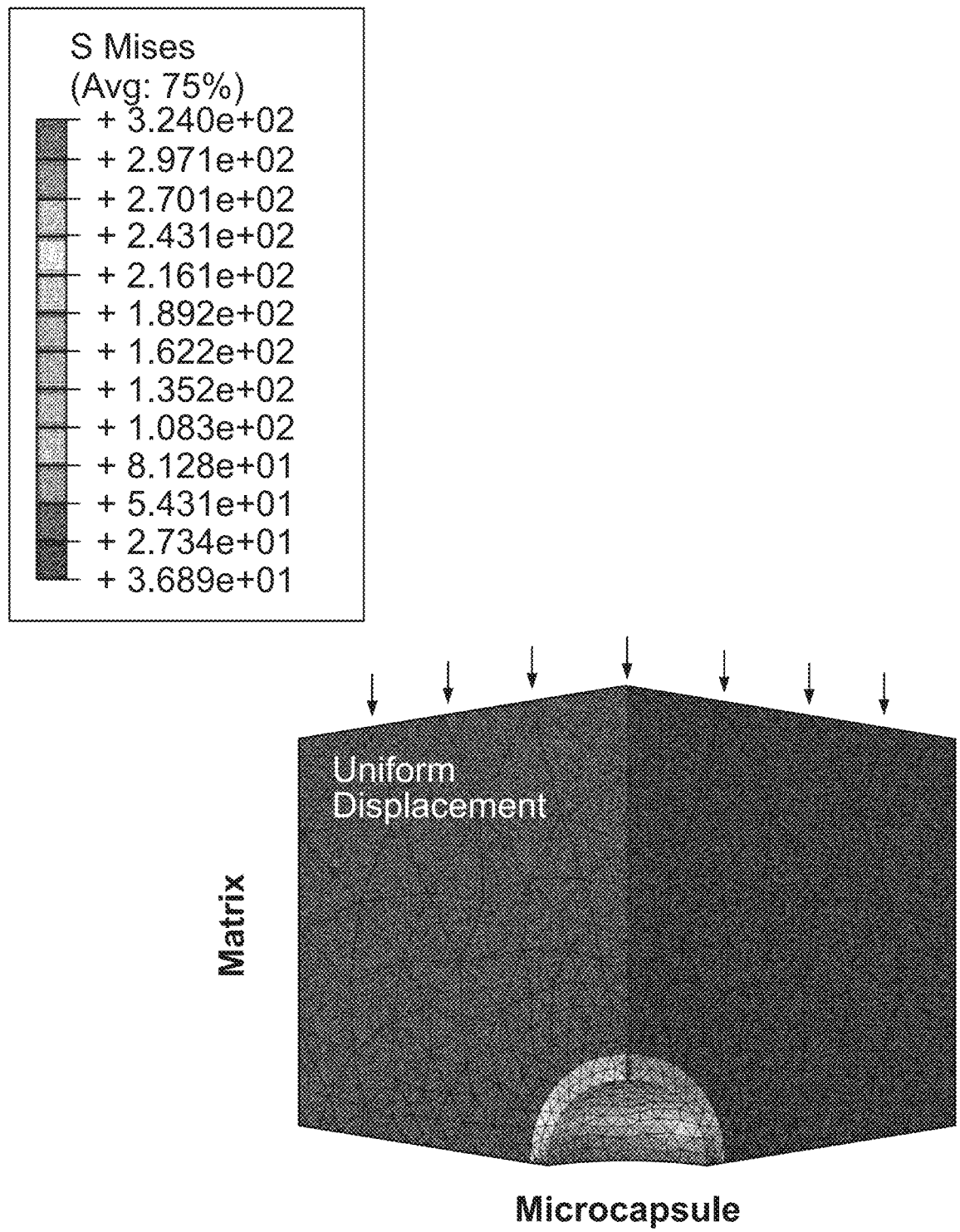
FIG. 8 illustrates field emission microscopy (FEM) of an embodiment of a gel-MAMC composite showing von Mises stress with gel deformation according to aspects of the present invention.

A similar methodology to that described in Example 3 was carried out to model engineered cartilage by embedding-microcapsules in PEGDA hydrogel. The PEGDA hydrogel has mechanical properties that can be tuned to mimic immature or mature engineered cartilage. Uniaxial compression on a confocal mounted device (FIG. 7A) was applied to the MAMCS embedded in the hydrogel at increments of 5% to 20% strain. See FIG. 9C. Microcapsule strain was quantified in the direction of the uniaxial strain (E11) or perpendicular to the direction of the uniaxial compression (E22). See FIG. 9A. FIG. 8 is a diagram depicting field emission microscopy (FEM) of an embodiment of a gel-MAMC composite showing von Mises stress with gel deformation, and the strain profile placed upon an embedded microcapsule as a result of uniform compression 1. Adhesion.

In conventional self-healing polymers, strong interfacial adhesion between microcapsules and the matrix is critical for promoting capsule rupture upon crack formation. A rough exterior shell wall, decreasing capsule shell-to-radius ratio, and the nature of adhesive interaction (e.g., electrostatic vs. protein-ligand interactions) can influence rupture. For embedded MAMCs, the ratio of the elastic modulus of embedding matrix to that of shell may determine whether crack propagation occurs through or deflects around microcapsules. During fabrication of MAMCs, adhesion properties can be tuned. For immediate release, as in cartilage repair after injury, the PLGA microcapsule shell will be generated using a polymerizable or cross-linkable surfactant (e.g., pluronic diacrylate, as a non-limiting example) as a stabilizer in double emulsion preparation. Pluronic diacrylate, if used, can be synthesized using a previously reported method, and can covalently bond microcapsules to the hydrogel upon photopolymerization. Alternatively, adhesion can be controlled using electrostatic interactions where either the shell or hydrogel is modified with a surface charge (e.g., PLGA-g-PLL) with a positive charge attracted to a negatively charged hydrogel. For delayed release scenarios with pre-culture of engineered cartilage prior to mechanically-induced release, it may be possible to rely on cell adhesion and matrix deposition on a positively charged shell for strong matrix adhesion. Optimizing this parameter may be important for reliably predicting microcapsule rupture in various matrices and loading environments, and may allow for tuning the rupture sensitivity of MAMCs embedded in 3D matrices.

2. Ratio of Shell:Matrix Elasticity.

To evaluate the rupture of microcapsules in 3D gels with varying properties, MAMCs with defined shell moduli (based on AFM results) can be embedded in different matrices (e.g., acellular photo-crosslinked methacrylated hyaluronic acid (HA) or poly(ethylene glycol) diacrylate (PEGDA) hydrogels). HA and PEGDA hydrogels have been produced with compressive moduli spanning 5-2000 kPa. This allows for the ratio of the modulus of the shell to that of the surrounding matrix to be altered across a wide range. Previous models for autonomic self-healing materials (where release of a catalyst from a microcapsule initiates polymerization) have demonstrated that this ratio determines whether cracks are deflected around ($E_{shell}=3E_{matrix}$) or directed to microcapsules ($E_{shell}=\frac{1}{3}E_{matrix}$) to cause rupture. This ratio influences the design of MAMCs targeted to rupture under specific physiological loading (e.g., dynamic compressive loading vs. singular compressive injury). MAMCs can be designed to rupture across matrix moduli representative of engineered cartilage as it matures (about 50 to 600 kPa).

In one methodology, microcapsules were embedded in two different PEGDA hydrogel compositions having different levels of stiffness (50 kPa versus 500 kPa). The two PEGDA hydrogel composites have mechanical properties tuned to mimic immature cartilage (50 kPa) and mature cartilage (500 kPa). See FIGS. 9A and 9B. Microcapsule strain was quantified in the direction of the uniaxial strain ($E_{11}$) or perpendicular to the direction of the uniaxial compression ($E_{22}$). Microcapsules embedded within the softer matrix (50 kPa) experienced very little or no deformation under increasing strain to the matrix, and even upon fracture the shell of the microcapsules show only minimal deformation. In contrast, microcapsules embedded in a matrix having a stiffness ten-fold higher (500 kPa) deformed significantly over increasing strain, with folds developing in the shell wall. The microcapsules were permanently deformed upon hydrogel fracture as well. See FIGS. 9A and 9B. Additionally, previous experiments found that MAMCs ruptured in 30% PEGDA hydrogels that had an elastic modulus of about 1.9 MPa (about 2-fold stiffer than in vitro engineered cartilage).

3. Micromechanical Analyses and FE Modeling.

Deformation of MAMCs embedded in a hydrogel may be measured using a custom compression device mounted on a confocal microscope (FIG. 7A). Briefly, constructs are subjected to compression in a step strain manner at intervals of 4% to a total of 20% strain, with a hold of about 30 minutes between steps to allow for release from ruptured MAMCs. Additional samples may be subjected to a single loading event representative of a compressive injury. Image stacks (~500 µm) can be reconstructed to visualize MAMC deformation and to determine deformation thresholds for release. For each MAMC formulation, "dose-response curves" are constructed by correlating applied strain to the fraction of ruptured MAMC. For a given "physiologic" strain (i.e., 10%, used in long-term loading studies), the same analysis is performed with cyclic deformation to determine number of cycles before rupture (i.e., to demonstrate rupture after fatigue). From these curves, loading conditions that elicit rupture of 1 of the MAMCs for a given matrix elasticity can be determined. To further this analysis, FE models of MAMC-gel composites may be developed. While analytical solutions exist to predict stress/strain in the matrix and the shell of a spherical inclusion, FE models provide a versatile means by which to infer the fracture behavior of MAMCs with variation in multiple parameters. FE models can be built in Abaqus, and geometry, boundary conditions (microcapsule-matrix adhesion), dimensions, and material properties of shell and matrix explored. Deformation behavior MAMCs at small strains (FIG. 8) can therefore be predicted, and may guide the design of MAMCs with different rupture behaviors with loading.

A series of MAMC/gel composites can therefore be generated, demonstrating controlled release in response to different mechanical perturbation (single compression injury, stepwise compression, and/or dynamic loading or fatigue over cycles of loading and unloading). By varying MAMC physical characteristics, gel elasticity, and interaction of MAMCs with the gel, we can identify and generate MAMC sets that rupture at different stages of tissue maturation and in response to physiologic and pathophysiologic loading.

Example 5. Demonstrating that Biologics Released from MAMCs can Stimulate Maturation, Repair, and/or Disease Control in Response to Physiologic and Pathophysiologic Loading In this example, the effect of on-demand delivery of biologics from MAMCs on altering the trajectory of tissue growth and/or repair, or disease modification and/or control, in engineered cartilage constructs is studied. MAMCs are first embedded in hydrogel constructs and activated by loading to release factors to promote tissue formation. Factors may be any biologics or molecules capable of acting as therapeutics in mechanically-loaded musculoskeletal tissues. These factors include, but are not limited to, chondrogenic factors, anabolic compounds, transforming growth factors (e.g., TGF-β, TGF-α), fibroblast growth factors (e.g., FGF-2, FGF-18), connective tissue growth factors (e.g., CTGF), insulin-like growth factors (e.g., IGF-1), and bone morphogenetic proteins (e.g., BMP-2, BMP-6). Other factors include anti-catabolic, anti-inflammatory, or anti-cell death compounds or biological therapeutics that may be used to control or modify diseases in mechanically-loaded musculoskeletal tissues.

This example can be used to specifically determine whether load-induced release of transforming growth factor beta (TGF-β) is capable of instigating the chondrogenic differentiation of mesenchymal stem cells (MSCs). TGF-β is also known to induce cartilage tissue formation and plays an important role in cartilage repair and the repair of other musculoskeletal tissues. Second, this may illustrate the therapeutic potential of MAMCs tuned to release with pathophysiologic loading, using a model of post-traumatic osteoarthritis (PTOA). Embedded microcapsules in constructs can be tuned to rupture upon injurious compression, and the effect of local release of anti-catabolic and/or anabolic compounds may be evaluated in terms of attenuation of matrix loss and reduction of protease activity in the tissue.

1. Programmed Release to Induce Chondrogenesis.

Figure 10:
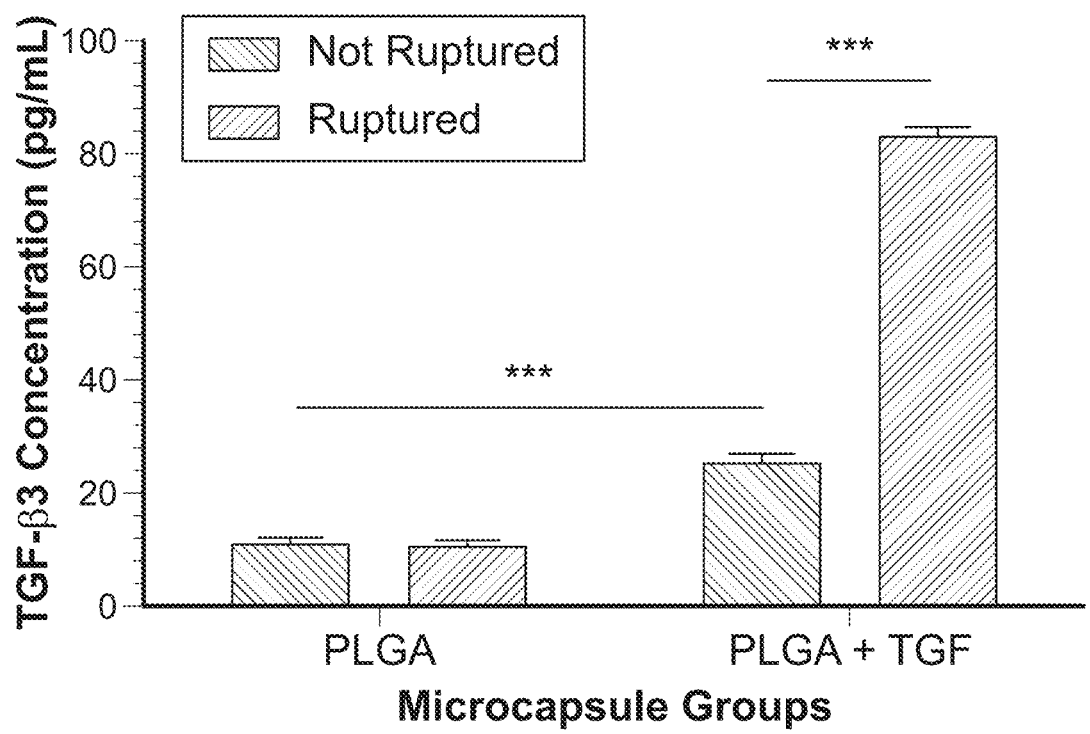
FIG. 10 illustrates active TGF-β3 release from ruptured MAMCs having poly(lactic-co-glycolic)acid shells embedded in hydrogel matrix, according to aspects of the present invention.

Engineered cartilage is formed by encapsulating MSCs in photo crosslinked 1% HA hydrogels. In the absence of chondrogenic factors, MSCs in HA gels do not differentiate or produce cartilage-like matrix. Here, hydrogels include MAMCs having PLGA shells loaded with the chondrogenic factor TGF-β3. See FIG. 10. TGF-β3 release from embedded microspheres (100 ng TGF/construct) can induce chondrogenesis. For these studies, TGF concentration in the core of the MAMCs may be defined so as to place 100 ng per construct, based on the MAMC volume fraction (10/0 v/v). Constructs with blank PLGA MAMCs (containing only PBS) are used as negative controls. Medium supplemented with TGF (100 ng/construct, distributed evenly over each media change) may serve as a positive control. The supernatant was analyzed by ELISA for released TGF-β3. Active TGF-β3 release was observed from ruptured MAMCs, with minimal leakage from non-ruptured MAMCs.

Based on Example 4, MAMCs may be selected to achieve complete rupture, partial rupture, and no rupture over the course of tissue maturation. From previous experiments, engineered constructs cultured over 4 weeks achieve equilibrium moduli of about 50-100 kPa, and dynamic moduli of about 500-1000 kPa. Based on this, the inventors hypothesize that microcapsules with an elastic modulus about ⅓ of that of the matrix are likely to ensure complete release, while an elastic modulus approximately equal to the matrix will result in partial release, and about 3-fold higher elastic modulus than the matrix will result in no release. To verify release, cell-free HA gels of varying weight percent (1-10% w/v), having equilibrium and dynamic properties spanning the range of tissue maturation, are used. In cell-based experiments, constructs are subjected to dynamic compression (10% strain, 1 Hz, 3 hours per day, 5 days per week) to simulate physiologic loading. Free-swelling constructs with embedded MAMCs may serve as controls, with no microcapsule rupture expected to occur. Constructs can be cultured for up to four weeks, with weekly harvest (n=5) to evaluate MSC differentiation. Differentiation can be assessed by Alcian blue staining of proteoglycan (PG) deposition and measurement of biochemical content (PG and collagen) and mechanical properties, as in previous studies. MAMC properties are expected to correlate with growth factor release with load and that, in cell-based constructs, release is expected to drive chondrogenesis.

2. Programmed Release after Injury.

An engineered cartilage model of injurious compression was developed to investigate mechanisms of degeneration in PTOA using a high throughput mechanical injury device for testing compressive injury of engineered cartilage. Based on this model, chondrocytes can be encapsulated in HA and pre-cultured for 8 weeks, followed by injury. MAMCs are embedded in the constructs at the time of formation. Here, MAMCs with elastic properties that are more compliant than a mature construct (e.g., $E_{hydrogel}$=300-500 kPa at 8 weeks, $E_{shell} \ll E_{hydrogel}$) can be used to guide crack propagation through the microcapsules. Pre-matured constructs are subjected to injurious compression (50% strain at 50%/s). After injury, chondrocyte viability decreases and loss of matrix increases. To determine whether MAMCs can alter these outcomes following injury, two potential therapeutics are included during MAMC fabrication: an anti-catabolic compound (MMP inhibitor doxycycline) to reduce degradation, and an anabolic compound (TGF-β) to increase matrix biosynthesis. The effectiveness of TGF-β (10 ng/mL) in reducing GAG loss (by about 30% 5 days post-injury) compared to injured controls has been shown. Low doses of TGF-β (10 ng/mL) and doxycycline (50 ng/mL) also reduce MMP activity after inflammatory stimulation of chondrocytes. Based on this, the activity of these factors is first validated by testing doses of 10 to 100 ng/construct. MAMCs are produced with factors at these doses and constructs are injured and analyzed at 48 and 120 hours. Both un-injured constructs with embedded MAMCs and blank MAMCs serve as controls. At each time point post injury, sulfated glycosaminoglycan (s-GAG), present in the construct and released to the media, is assayed (n=4). Additional samples may stained for viability (Live/Dead) and proteoglycans (Alcian blue). In addition, MMP inhibition can be evaluated by immunostaining for neo-epitopes engendered by MMP activity (n=3) and active MMP can be assayed in the media (Anaspec). As above, ELISA can be used to measure TGF-β release after injury.

The inventors hypothesize that MAMCs can be tuned to release TGF-beta over the course of construct maturation for MSC-seeded hydrogels, and this release can induce chondrogenesis and matrix accumulation. In the context of injurious compression, immediate release from microcapsules is expected, enhancing cell viability post-injury and attenuating loss of proteoglycan from constructs.

The embodiments described herein are intended to be exemplary of the invention and not limitations thereof. One skilled in the art will appreciate that modifications to the embodiments and examples of the present disclosure may be made without departing from the scope of the present disclosure.

The invention claimed is:

1. A method of using mechanically-activated microcapsules (MAMCs) for drug delivery, comprising:
    delivering, to a joint of a subject's body, a population of MAMCs,
        the MAMCs comprising one or more active ingredients contained therein, and
        the population of MAMCs having one or more rupture profiles such that force developed within the joint during the joint's physiologic activity gives rise to rupture of the MAMCs in response to a physiologic mechanical load exerted by the joint on the population of MAMCs during the joint's physiologic activity,
        wherein a rupture profile is associated with a minimum mechanical load applied to a MAMC that ruptures the MAMC such that the MAMC's contents are released into the surrounding environment; and
    rupturing the MAMCs by the physiologic activity of the joint.

2. The method of claim 1, wherein a first subpopulation of the population of MAMCs has a first rupture profile, wherein a second subpopulation of the population of MAMCs has a second rupture profile, and wherein the first rupture profile and the second rupture profile have different minimum mechanical loads.

3. The method of claim 2, wherein the MAMCs of the first subpopulation define a first shell thickness, wherein the MAMCs of the first subpopulation define a second shell thickness, and wherein the first and second shell thicknesses differ from one another.

4. The method of claim 2, wherein the MAMCs having the first rupture profile are delivered to the subject's body at a different time than the MAMCs having the second rupture profile.

5. The method of claim 1, wherein some of the population of MAMCs comprise a first active ingredient and some of the population of MAMCs comprise a second active ingredient.

6. The method according to claim 1, wherein delivering the MAMCs to said joint of the subject's body comprises injecting the MAMCs into said joint.

7. The method according to claim 6, comprising delivering the MAMCs to a knee joint, elbow joint, shoulder joint, wrist joint, ankle joint or hip joint.

8. The method according to claim 1, wherein the MAMCs are embedded within a matrix material, and wherein delivering the MAMCs to said joint of the subject's body comprises implanting the matrix material into said joint.

9. The method of claim 8, wherein the matrix material comprises a hydrogel.

10. The method of claim 8, wherein the MAMCs are covalently bonded to the matrix material.

11. The method of claim 8, wherein the MAMCs are electrostatically bonded to the matrix material.

12. The method according to claim 1, wherein the one or more rupture profiles of the MAMCs enable the MAMCs to rupture after exposure to a single mechanical load.

13. The method according to claim 1, wherein the one or more rupture profiles of the MAMCs enable the MAMCs to rupture after multiple exposures to mechanical loads.

14. The method according to claim 1, wherein an active ingredient comprises an anti-catabolic compound, an anabolic compound, an anti-inflammatory compound, a chondrogenic factor, or a growth factor.

15. The method according to claim 14, wherein the active ingredient comprises at least one of transforming growth factors, fibroblast growth factors, connective tissue growth factors, insulin-like growth factors, or bone morphogenetic proteins.

16. The method according to claim 1, wherein the MAMCs comprise polymeric shells comprising poly(lactic-co-glycolic) acid (PLGA).

* * * * *